(12) United States Patent
Mhaske et al.

(10) Patent No.: US 9,518,051 B2
(45) Date of Patent: Dec. 13, 2016

(54) PYRROLOQUINOLINE ALKALOIDS AS ANTIMALARIAL AGENTS AND PROCESS FOR THE PREPARATION THEREOF

(71) Applicant: Council of Scientific & Industrial Research, New Delhi (IN)

(72) Inventors: Santosh Baburao Mhaske, Maharashtra (IN); Jyoti Reveji Lande, Maharashtra (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 14/377,407

(22) PCT Filed: Feb. 8, 2013

(86) PCT No.: PCT/IB2013/000164
§ 371 (c)(1),
(2) Date: Aug. 7, 2014

(87) PCT Pub. No.: WO2013/117986
PCT Pub. Date: Aug. 15, 2013

(65) Prior Publication Data
US 2015/0336947 A1    Nov. 26, 2015

(30) Foreign Application Priority Data
Feb. 8, 2012 (IN) .............................. 356/DEL/2012

(51) Int. Cl.
*C07D 471/04* (2006.01)
*C07D 519/00* (2006.01)

(52) U.S. Cl.
CPC ........... *C07D 471/04* (2013.01); *C07D 519/00* (2013.01)

(58) Field of Classification Search
CPC .............................. C07D 471/04; C07D 519/00
See application file for complete search history.

(56) References Cited

PUBLICATIONS

Mahajan et al., Organic Letters, 2012, vol. 14, No. 22, 5804-5807.*
Anthony R. Carroll et al., "Aplidiopsamine A, An Antiplasmodial Alkaloid from the Temperature Australian Ascidian, Aplidiopsis Confluata," The Journal of Organic Chemistry, vol. 75, No. 23, Dec. 3, 2010, pp. 8291-8294.
Patrick W. Okanya et al "Marinoquinolnes A-F Pyrroloquinolines from Ohtaekwangia Kribbensis (Bacteroidetes)," Journal of Natural Products, vol. 74, No. 4, Apr. 25, 2011, pp. 603-608.
Lijun Ni et al., "Concise Total Syntheses of Marinoquinolines AC," Tetrahedron Letters, Elsevier Amsterdam, NL, vol. 53, No. 10, Dec. 30, 2011, pp. 1271-1274.
Thibaud Gerfaud et al., "Palladium-Catalyzed Annulation of Acyloximes with Arynes (or Alkynes): Synthesis of Phenanthridines and Isoquinolines," Angewandte Chemie International Edition, vol. 48, No. 3, Jan. 5, 2009, pp. 572-577.
Cristiane Storck Schwalm et al., "Divergent Total Synthesis of the Natural Antimalarial Marinoquoinolines A, B, C, E and Unnatural Analogues," Tetrahedron Letters, vol. 53, No. 36, Jul. 2, 2012, pp. 4836-4840.
Jyoti P. Mahajan et al., "PD-Catalyzed Imine Cyclization: Synthesis of Antimalarial Natural Products Aplidiopsamine A. Marinoquinoline A, and Their Potential Hybrid NCLite-M1," Organic Letters, vol. 14, No. 22, Nov. 16, 2012, pp. 5804-5807.
Joseph D. Panarese et al., "Biomimetic Synthesis and Biological Evaluation of Aplidiopsamine A," Organic Letters, vol. 14, No. 22, Nov. 16, 2012, pp. 5808-5810.
Xinghua Ma et al., "Total Synthesis of Marinoquinoline A Using a Palladium(0)-Catalyzed Ullmann Cross-Coupling Reaction," Asian Journal of Organic Chemistry, vol. 1, No. 2, 2012, pp. 160-165.

* cited by examiner

*Primary Examiner* — Sun Jae Yoo
(74) *Attorney, Agent, or Firm* — Blank Rome LLP; Michael C. Greenbaum

(57) ABSTRACT

The patent provides novel compounds with potential antimalarial activity and process of synthesis thereof. Further, the process for the synthesis of known antimalarial natural products marinoquinazolinone A-F, aplidiopsamine A and their potential antimalarial analogs is disclosed.

10 Claims, 21 Drawing Sheets

PYRROLOQUINOLINE ALKALOIDS AS ANTIMALARIAL AGENTS AND PROCESS FOR THE PREPARATION THEREOF

RELATED APPLICATIONS

This application is a National Phase of PCT/IB2013/000164, filed on Feb. 8, 2013, which claims priority to Indian Patent A cation 356/DEL/2012, filed Feb. 8, 2012, all of the disclosures of which are hereby incorporated by reference herein.

FIELD OF THE INVENTION

The present invention relates to field of novel compounds of the pyrroloquinoline alkaloids group and process for the preparation thereof. Particularly, the present invention relates to novel anti-malarial compounds and process of synthesis thereof. Further, the present invention also discloses the process for the synthesis of known antimalarial natural products Marinoquinoline A-F, Aplidiopsamine A and their potential antimalarial analogues.

BACKGROUND AND PRIOR ART

Alkaloids are highly important pharmacophores and currently available methods for the synthesis of substituted pyridine based alkaloids are tedious, lengthy and low yielding.

The natural products Marinoquinoline A-F, Aplidiopsamine A and related natural products have very good antimalarial activity but till date their synthesis is not known.

Sangoi et al in Marine Drugs, 2008, 6, 578-586 reports the acetylcholinerase-inhibiting activity of pyrrole derivatives obtained from a novel marine gliding bacterium, *Rapithidix thailandica*.

Gerfaud et al in Angew Chem Int, 2009, 48, 572-577 reported a process which leads to a rapid constriction of functionalized phenanthridines and isoquinolines by a domino aminopalladation/C-H functionalization sequence.

Carroll et al in JOC, vol 75, No: 23, 2010, 8291 describes Aplidiopsamine A isolated from the temperate Australian ascidian *Aplidiopsis confluata* and its anti-malarial properties.

But there is a need in the art to provide synthetic routes of synthesis of anti-malarial compounds isolated from natural resources such that therapies are available for drug resistant strains of *plasmodium*. It would be advantageous if such processes are simple, with reactants freely available and result in good yields and selectivity.

Further there is a continuous need for novel compounds that possess anti-malarial properties, such that clinicians have alternatives available to combat drug resistance in subjects infected with malaria.

OBJECT OF INVENTION

The main object of the present invention is to provide novel compounds of the pyrroloquinoline alkaloids group and process for the preparation thereof.

Another object of the invention is to provide novel compounds of the pyrroloquinoline alkaloids group that possess therapeutic activity.

Another object of the invention is to provide novel and efficient palladium catalyzed C—H activation methodology for the synthesis of substituted Pyrroloquinoline based alkaloids.

One more object of the present invention is to provide a process applicable to the total synthesis of antimalarial natural products and their potential analogs.

SUMMARY OF THE INVENTION

Accordingly, the present invention provides a compound of formula I,

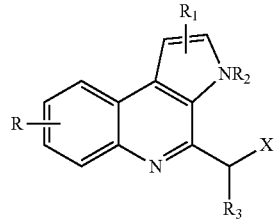

Formula I

Where R, $R_1$, $R_2$ are selected from H, halide, alkyl, aryl, hetero alkyl/aryl or heteroatom, X is selected from halide or activating groups such as H, OTf, OTs, $B(OR)_2$, $SnR_3$, $SiR_3$, and such like, and $R_3$ is selected from halide, or compound of formula III, wherein $R_4$ is selected from H, halide, alkyl, aryl, hetero alkyl/aryl, heteroatom.

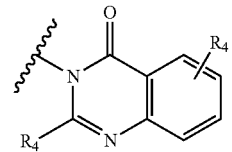

Formula III and its analogues, positional isomers, stereoisomers, derivatives, and pharmaceutically acceptable salt thereof.

In one embodiment of the present invention, a process for the preparation of compound of formula I,

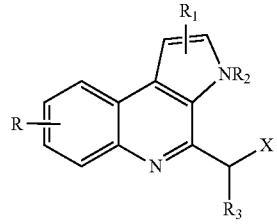

Formula I

R, $R_1$, $R_2$, $R_3$=H, halide, alkyl, aryl, hetero alkyl/aryl or heteroatom

X=H, halide or activating groups like H, OTf, OTs, $B(OR)_2$, $SnR_3$ or $SiR_3$.

and its analogues, stereoisomers, positional isomers, derivatives and pharmaceutically acceptable salt thereof comprising steps;

a. refluxing ketone and aniline in mole ratio 1:1 in a solvent preferably dry toluene for a period ranging between 12-24 hrs followed by work up to obtain corresponding imine;

b. Catalyzing the conversion of corresponding imine of step (a) in the presence of Pd catalyst, ligand, base and solvent at temperature ranging between 100-120° C. for a period between 8-24 hrs to obtain corresponding quinoline;

c. Catalyzing the conversion of compound 3 of step (b) to obtain corresponding substituted quinoline of formula I;

d. optionally, synthesizing Marinoquinoline compounds from product of step (b) by refluxing with potassium terbutoxide or methanol-$K_2CO_3$ at room temperature;

e. Synthesizing Aplidiopsamine A formed in step (c) by treatment with adenine and further deprotecting the $SO_2Ph$ group by methanol and $K_2CO_3$.

In an embodiment of the present invention The process according to claim 2, wherein the yield is in the range of 40% to 98%.

In another embodiment of the present invention the catalyst is preferably $Pd(OAc)_2$ in the range of 1 mol % to 20 mol % comprising a ligand.

In still another embodiment of the present invention the ligand is selected from triphenyl phosphate, $PPh_3$, Neocuproine, Tri cyclohexyl phosphine $PCy_3$, preferably $PPh_3$ in the range of 1 mol % to 40 mol %.

In yet another embodiment of the present invention the base is selected from $K_2CO_3$, $Cs_2CO_3$, $Ag_2CO_3$, KOtBu, preferably $Ag_2CO_3$ in the range of 1 mol % to 200 mol %.

In yet another embodiment of the present invention the solvent is chosen from 1,4-dioxane, di methy formamideDMF, Benzene, tetra hydro furan THF, preferably 1,4-dioxane.

In yet another embodiment of the present invention the catalyst is N-bromo succinimide NBS and radical initiators are Aza iso butyro nitrile (AIBN), Aza Bis cyanide (ABCN), preferably Benzyl peroxide (BPO) catalyzed N-bromo succinimide (NBS).

In yet another embodiment of the present invention a compound of formula I,

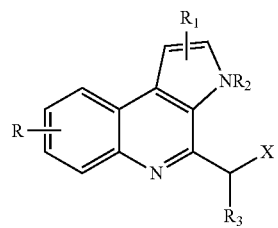

Formula I

Where R, $R_1$, —$R_2$ are selected from H, halide, alkyl, aryl, hetero alkyl/aryl or heteroatom, X is selected from halide or activating groups such as OTf, OTs, $B(OR)_2$, $SnR_3$, $SiR_3$, and such like, and $R_3$ is selected from halide, or compound of formula III, wherein $R_4$ is selected from H, halide, alkyl, aryl, hetero alkyl/aryl, heteroatom.

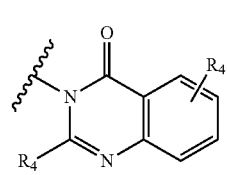

Formula III and its analogues, positional isomers, stereoisomers, derivatives, and pharmaceutically acceptable salt thereof useful as anti malarial agents.

In yet another embodiment of the present invention a compound of formula I,

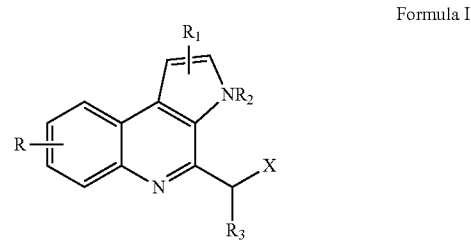

Formula I

Where R, $R_1$, —$R_2$ are selected from H, halide, alkyl, aryl, hetero alkyl/aryl or heteroatom, X is selected from halide or activating groups such as OTf, OTs, $B(OR)_2$, $SnR_3$, $SiR_3$, and such like, and $R_3$ is selected from halide, or compound of formula III, wherein $R_4$ is selected from H, halide, alkyl, aryl, hetero alkyl/aryl, heteroatom.

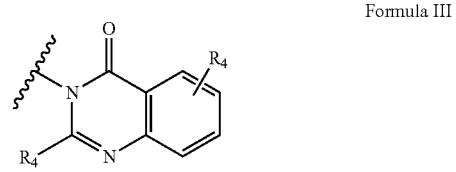

Formula III and its analogues, positional isomers, stereoisomers, derivatives, and pharmaceutically acceptable salt thereof useful as anti mycobacterial agents.

DETAILED DESCRIPTION OF THE INVENTION

Figure 1:
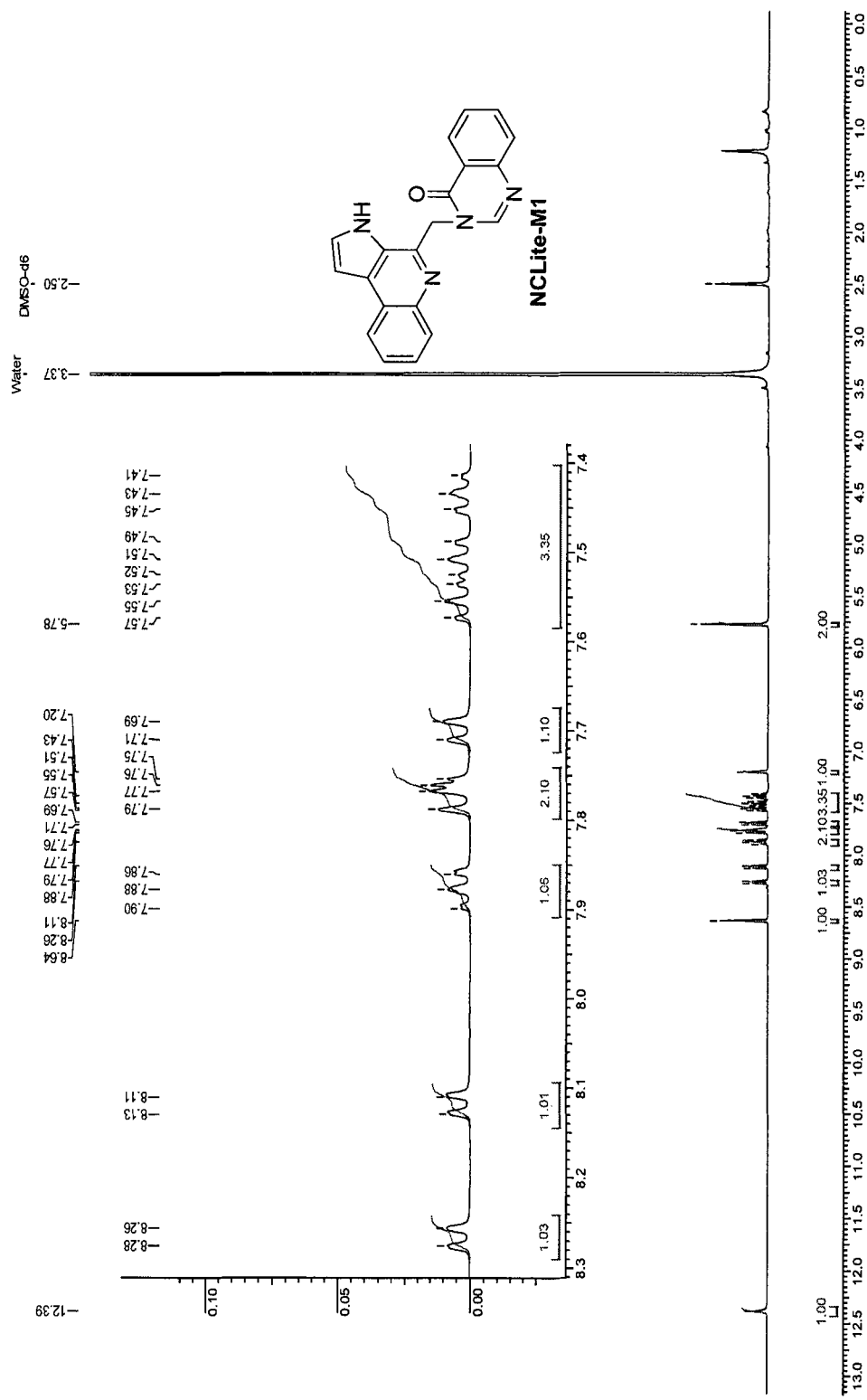
FIG. 1: $^1$H NMR spectra of compound 8
Figure 2:
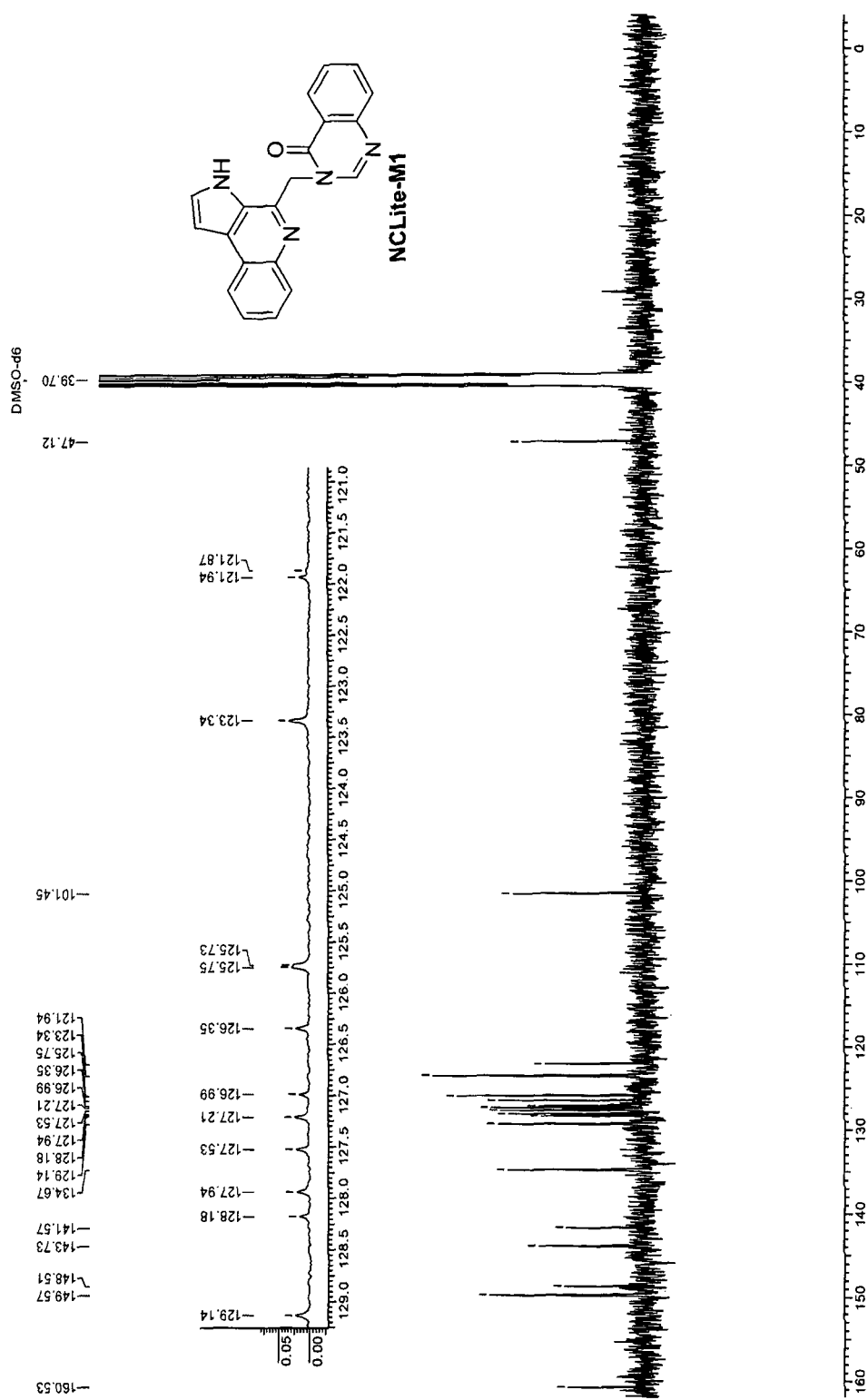
FIG. 2: $^{13}$C NMR spectra of compound 8
Figure 3:
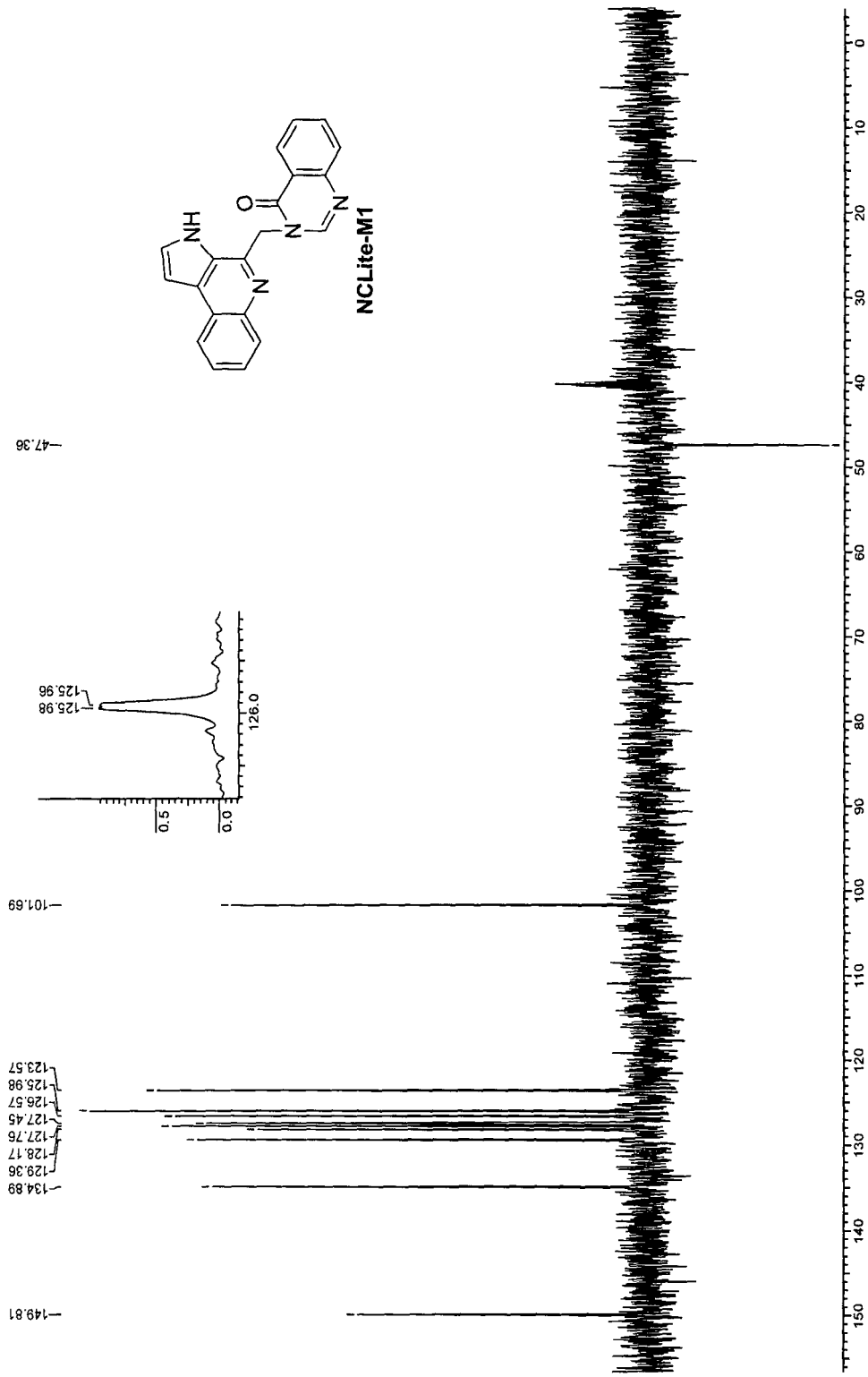
FIG. 3: DEPT NMR spectra of compound 8
Figure 4:
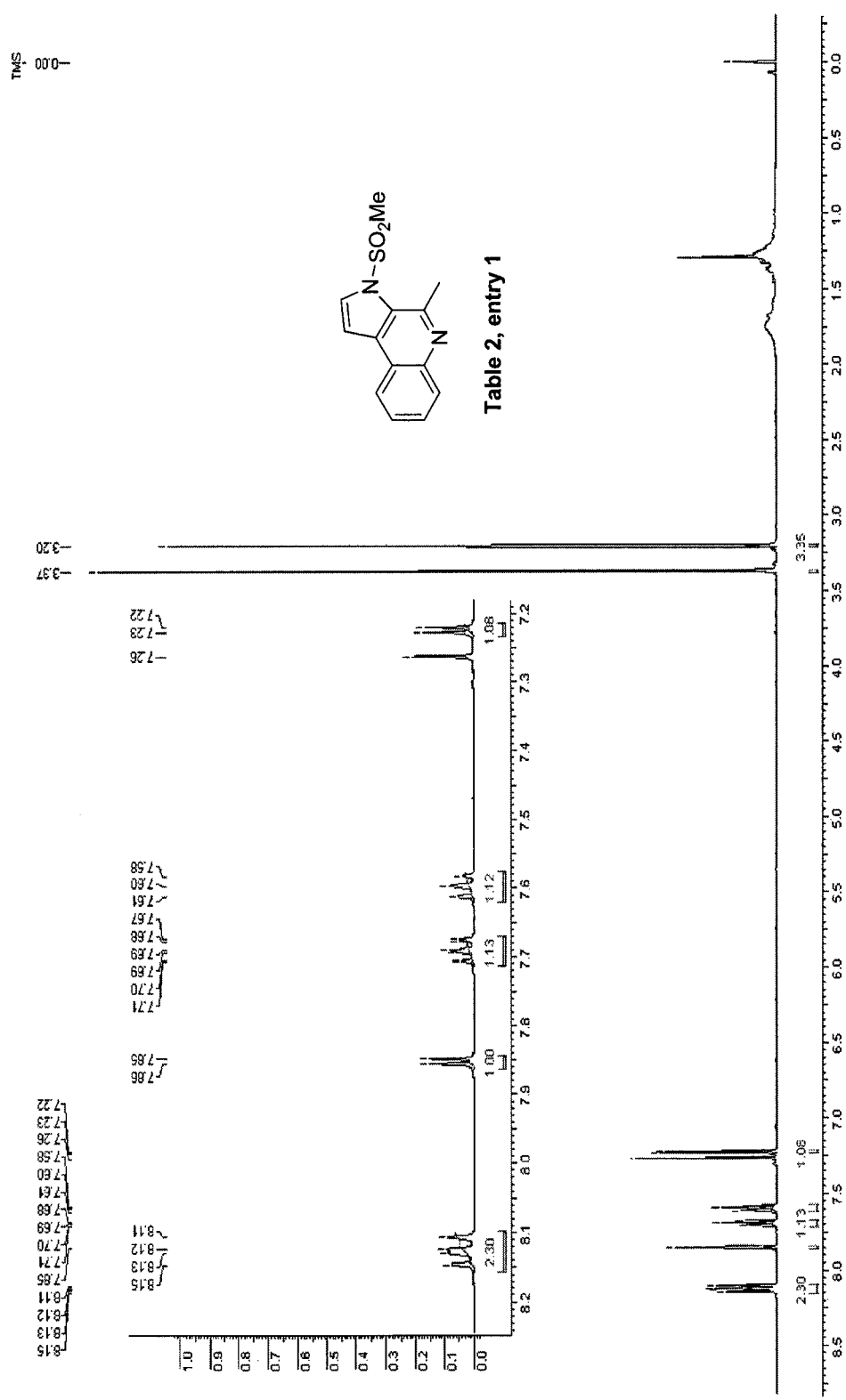
FIG. 4: $^1$H NMR spectra of compound of table 2, entry 1
Figure 5:
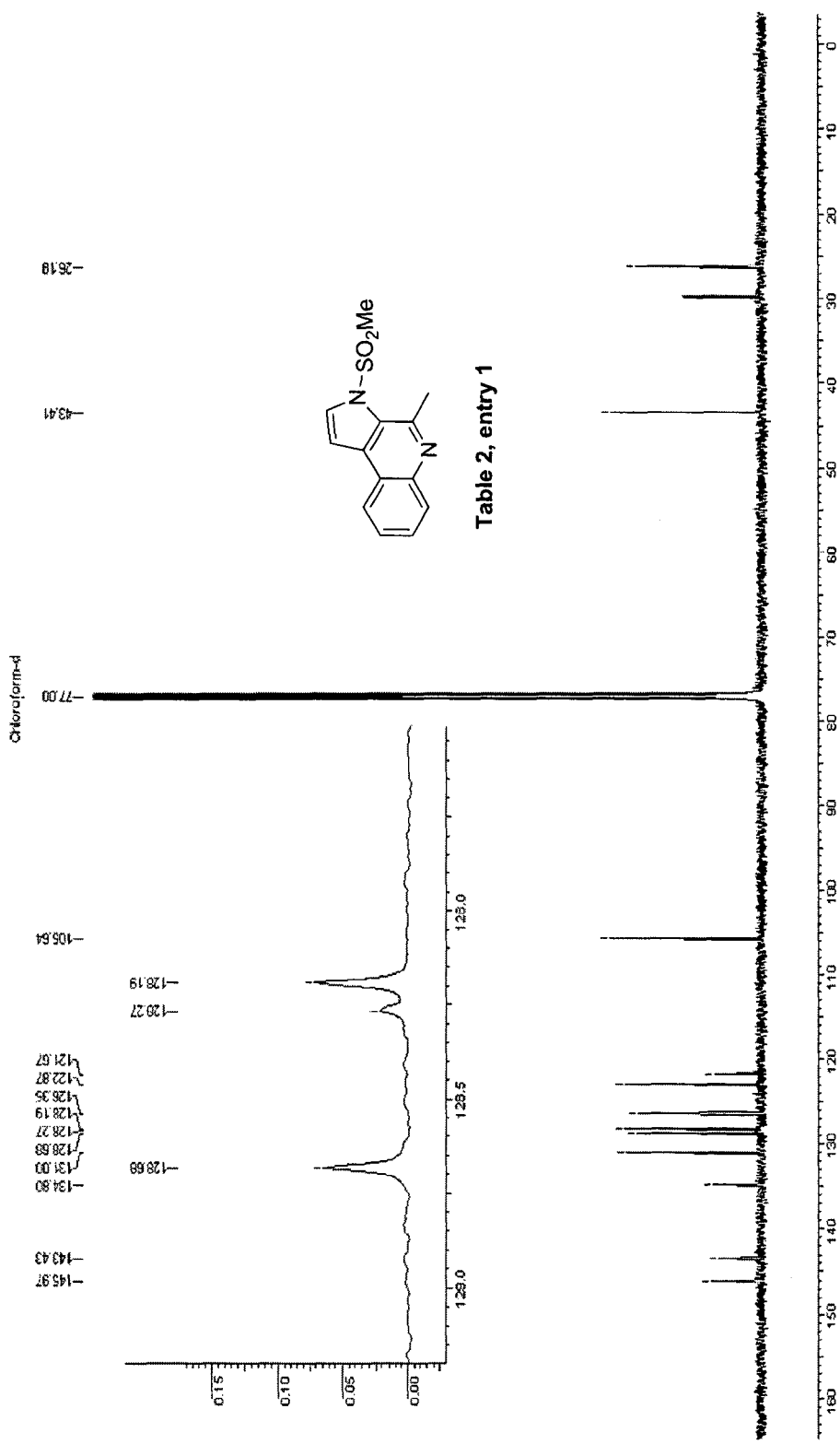
FIG. 5: $^{13}$C NMR spectra of compound of table 2, entry 1
Figure 6:
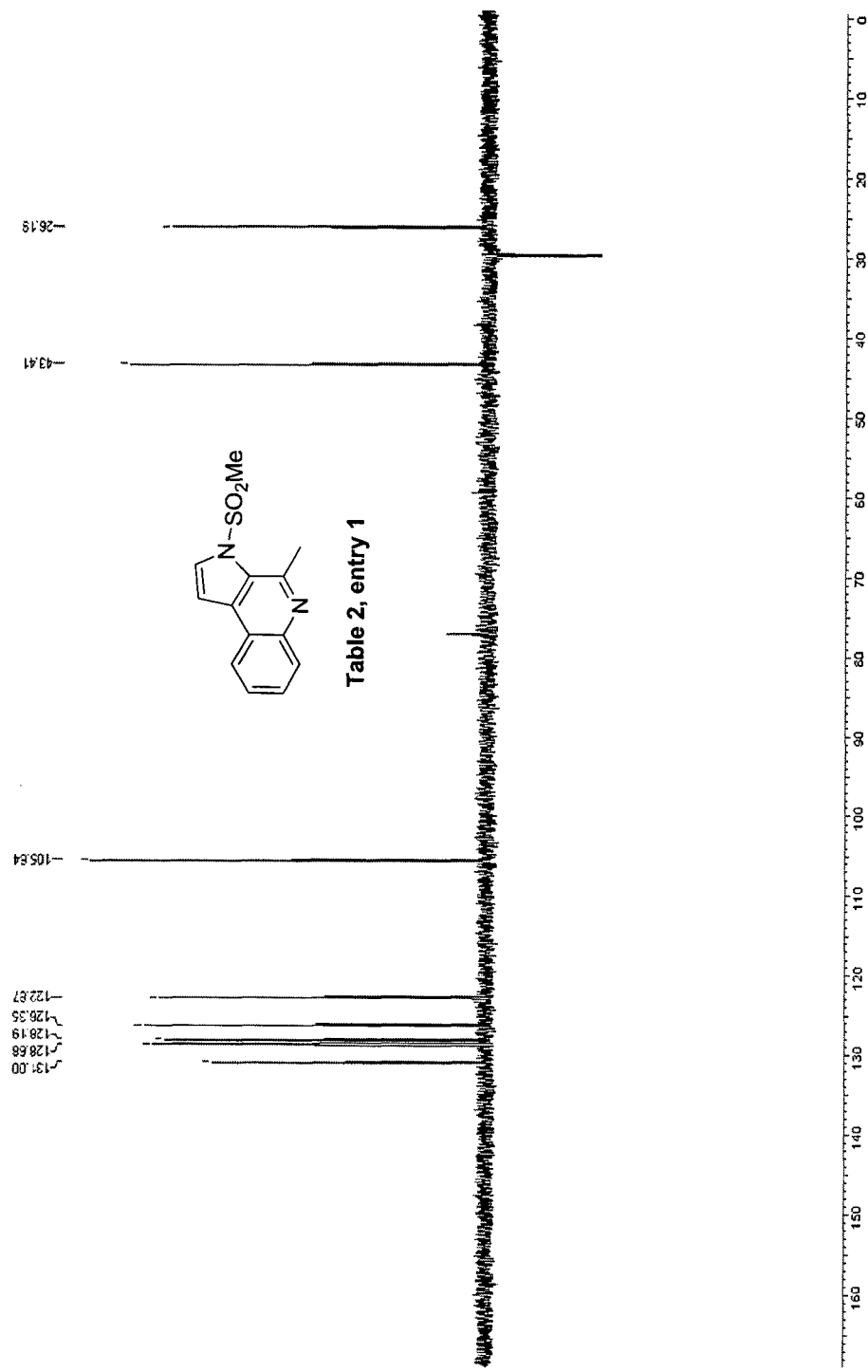
FIG. 6: DEPT NMR spectra of compound of table 2, entry 1
Figure 7:
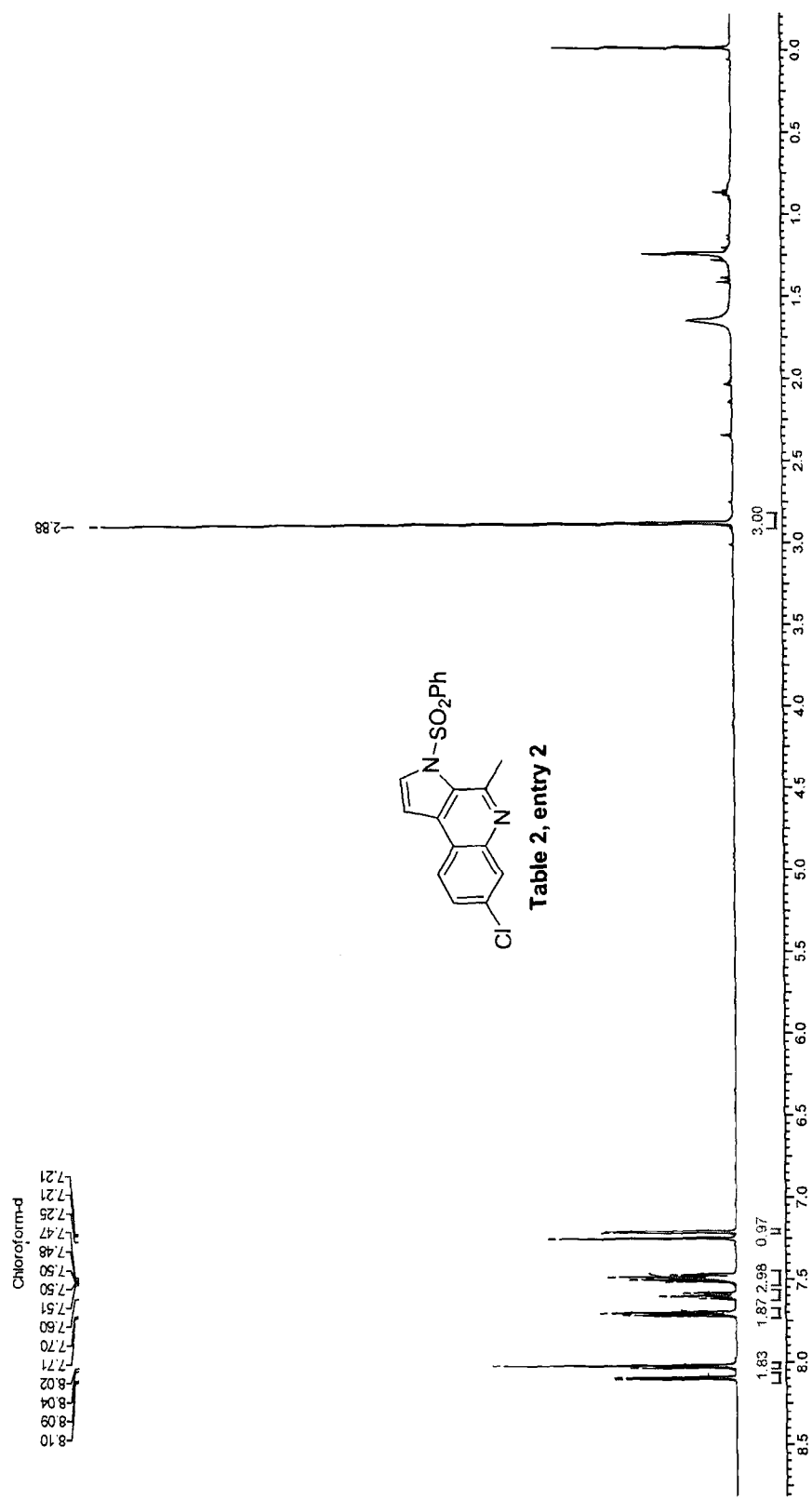
FIG. 7: $^1$H NMR spectra of compound of table 2, entry 2
Figure 8:
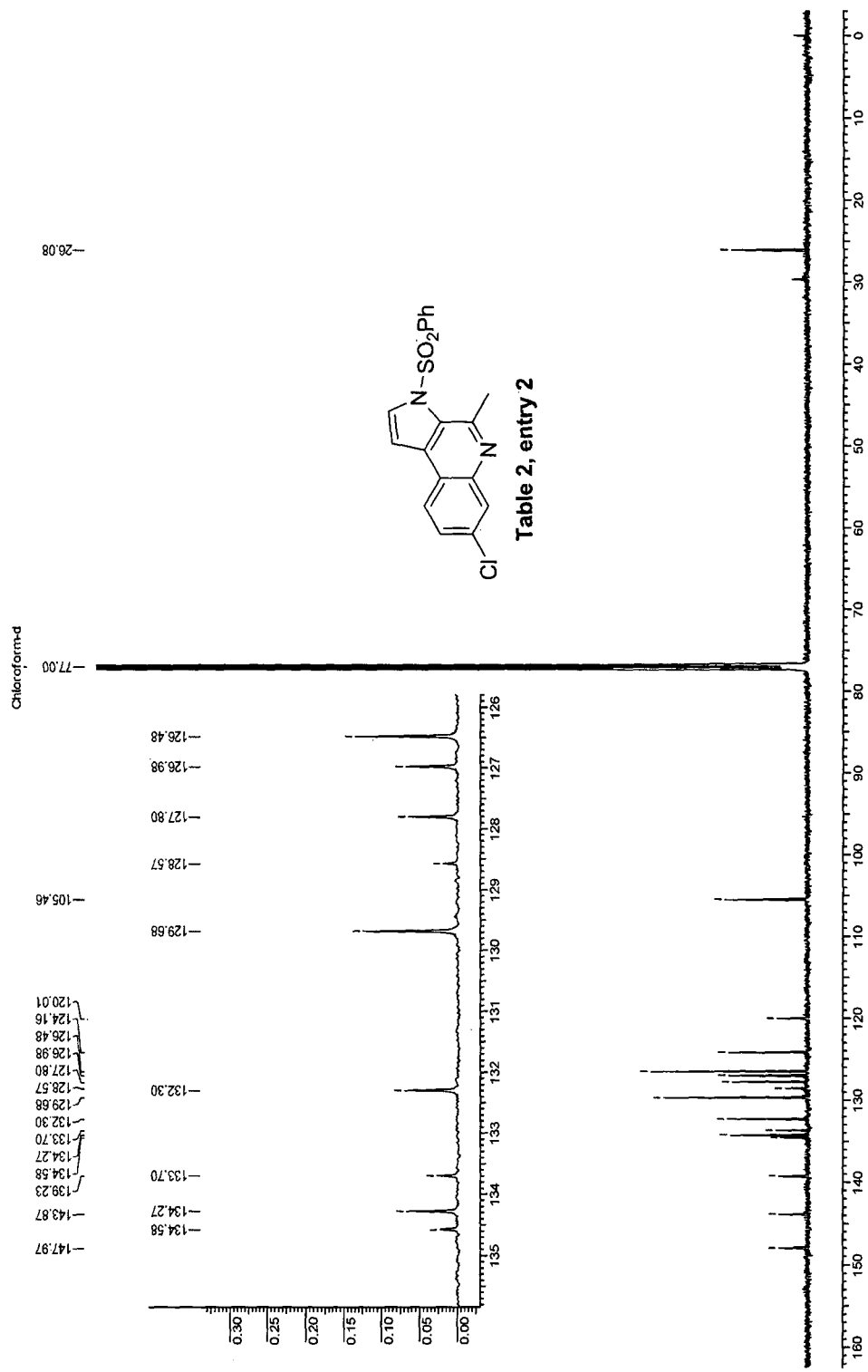
FIG. 8: $^{13}$C NMR spectra of compound of table 2, entry 2
Figure 9:
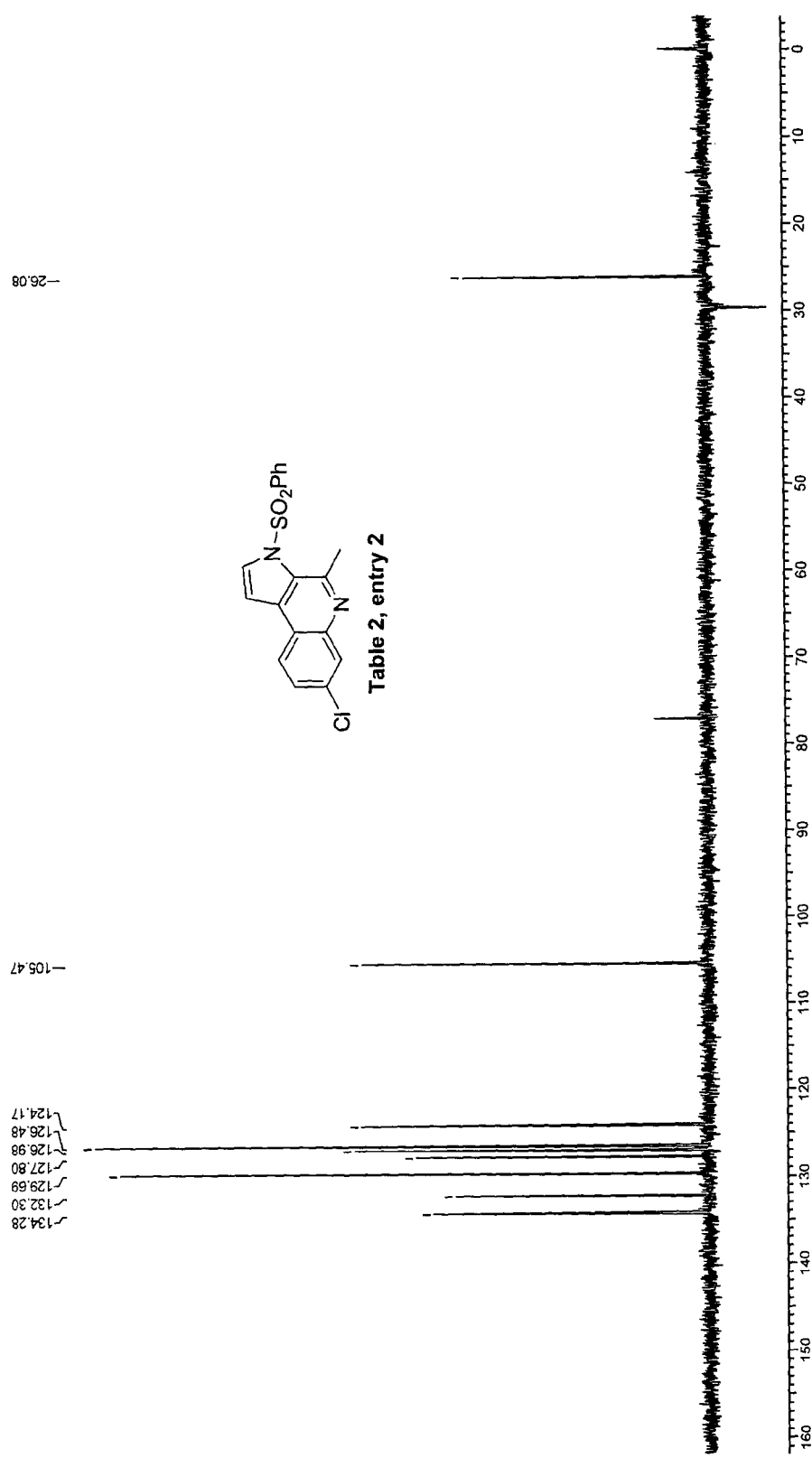
FIG. 9: DEPT NMR spectra of compound of table 2, entry 2
Figure 10:
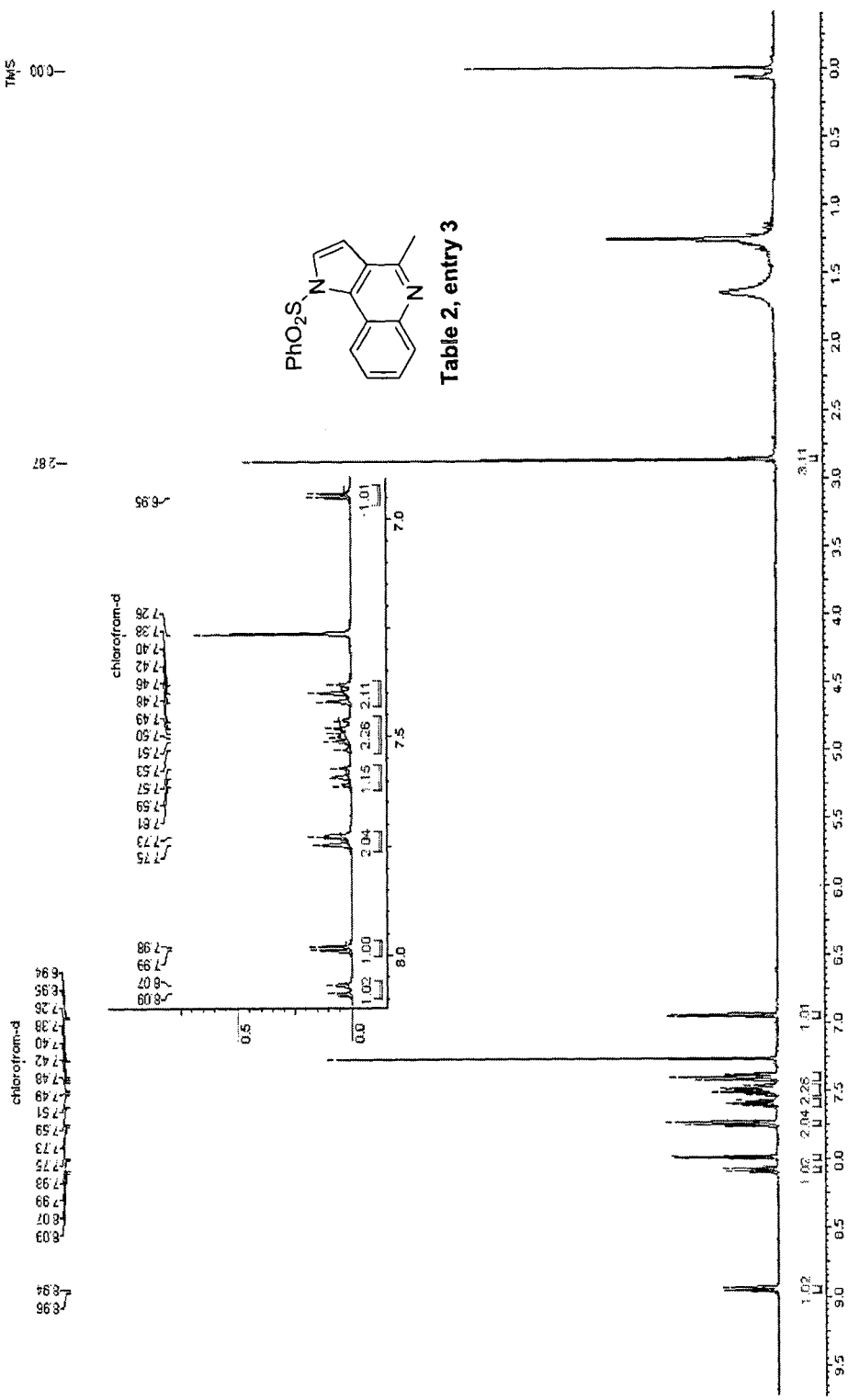
FIG. 10: $^1$H NMR spectra of compound of table 2, entry 3
Figure 11:
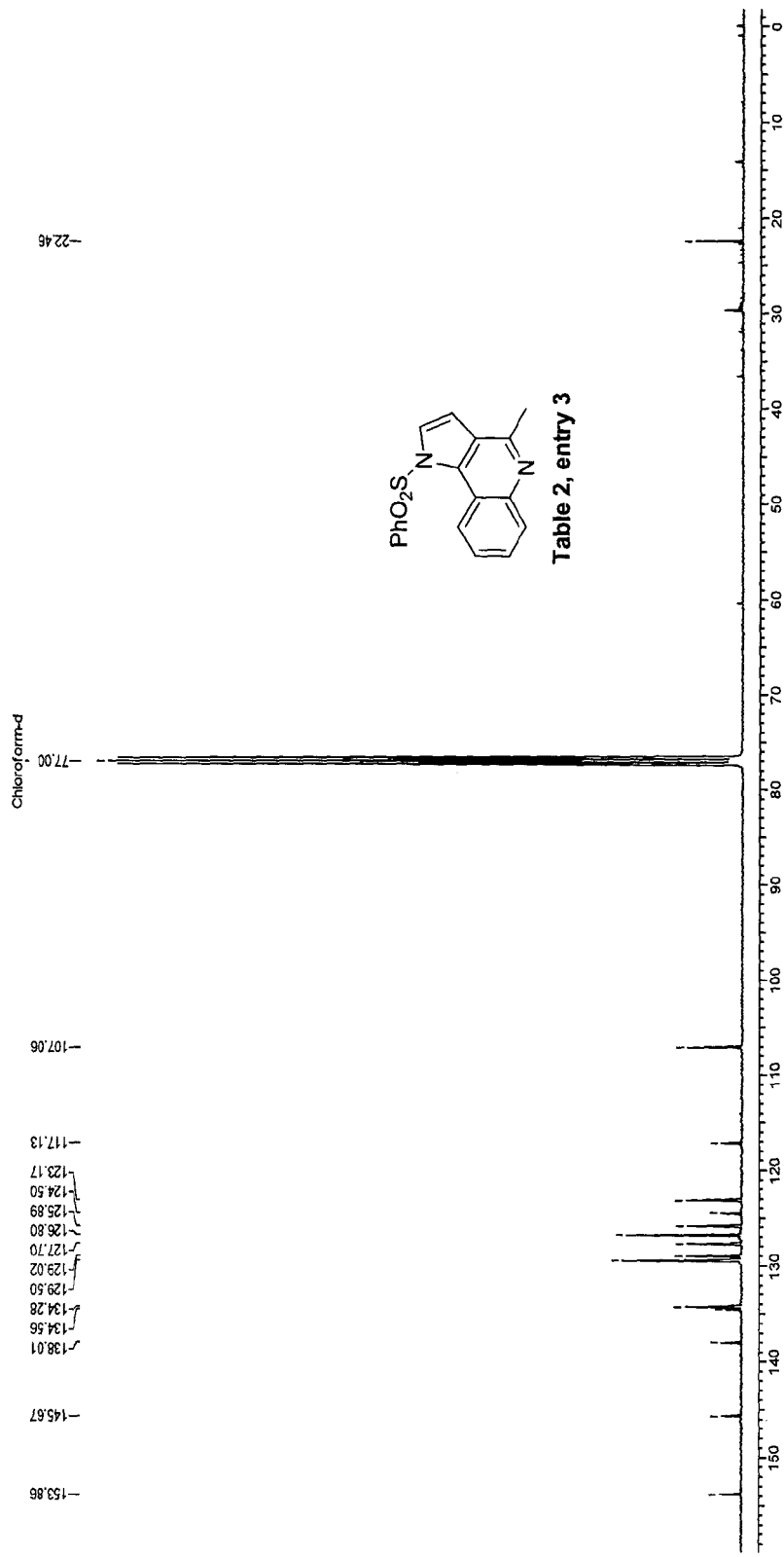
FIG. 11: $^{13}$C NMR spectra of compound of table 2, entry 3
Figure 12:
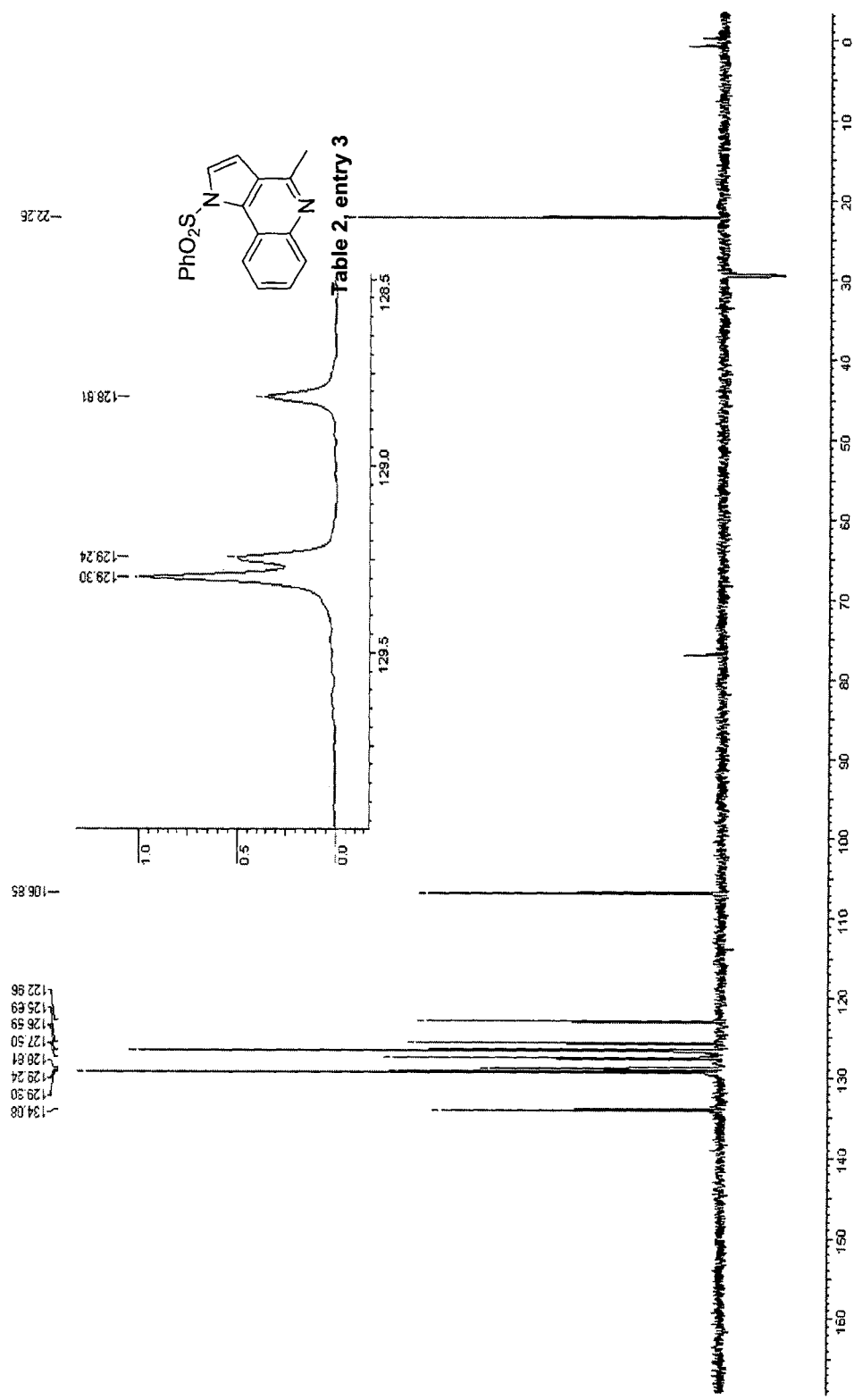
FIG. 12: DEPT NMR spectra of compound of table 2, entry 3
Figure 13:
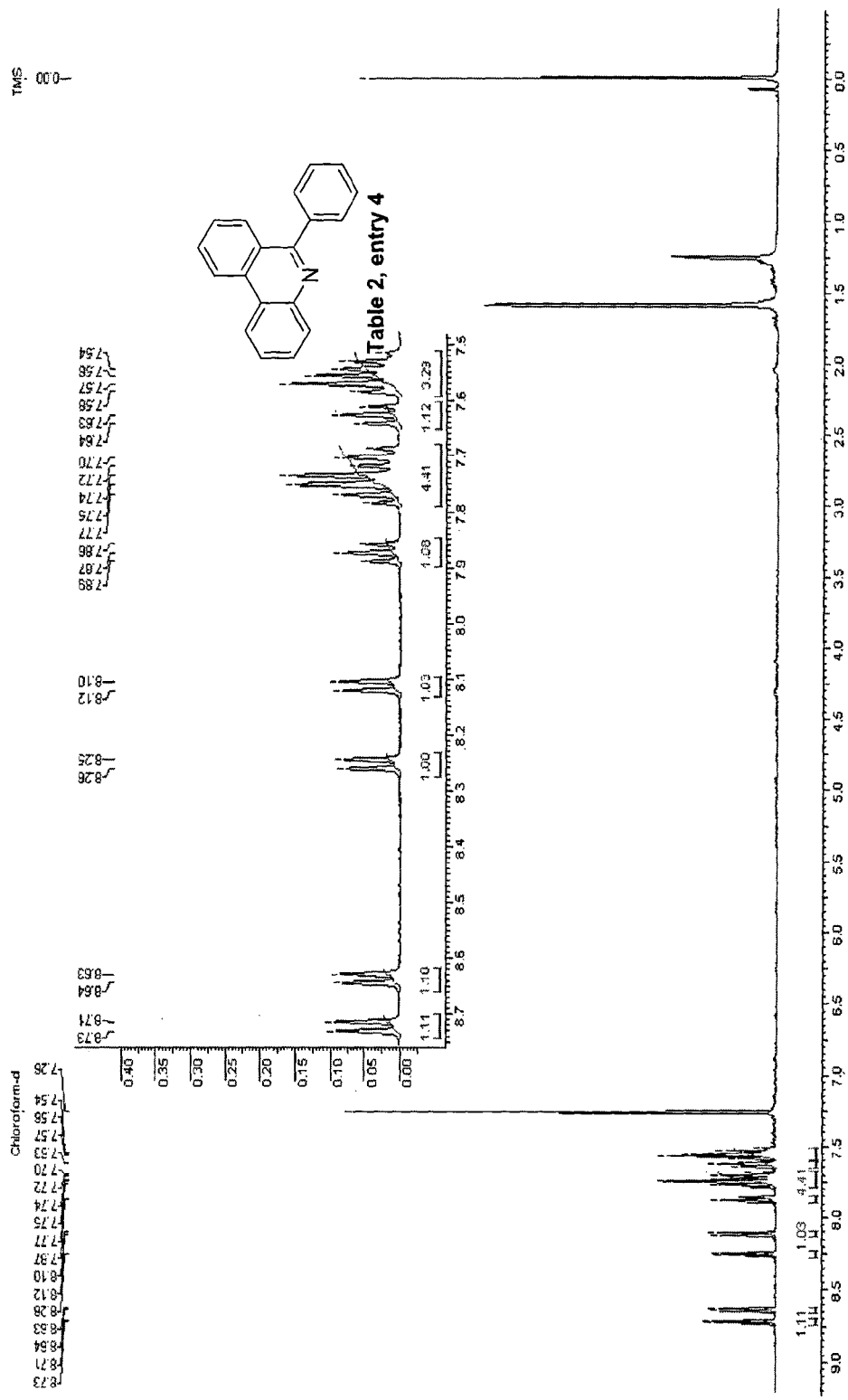
FIG. 13: $^1$H NMR spectra of compound of table 2, entry 4
Figure 14:
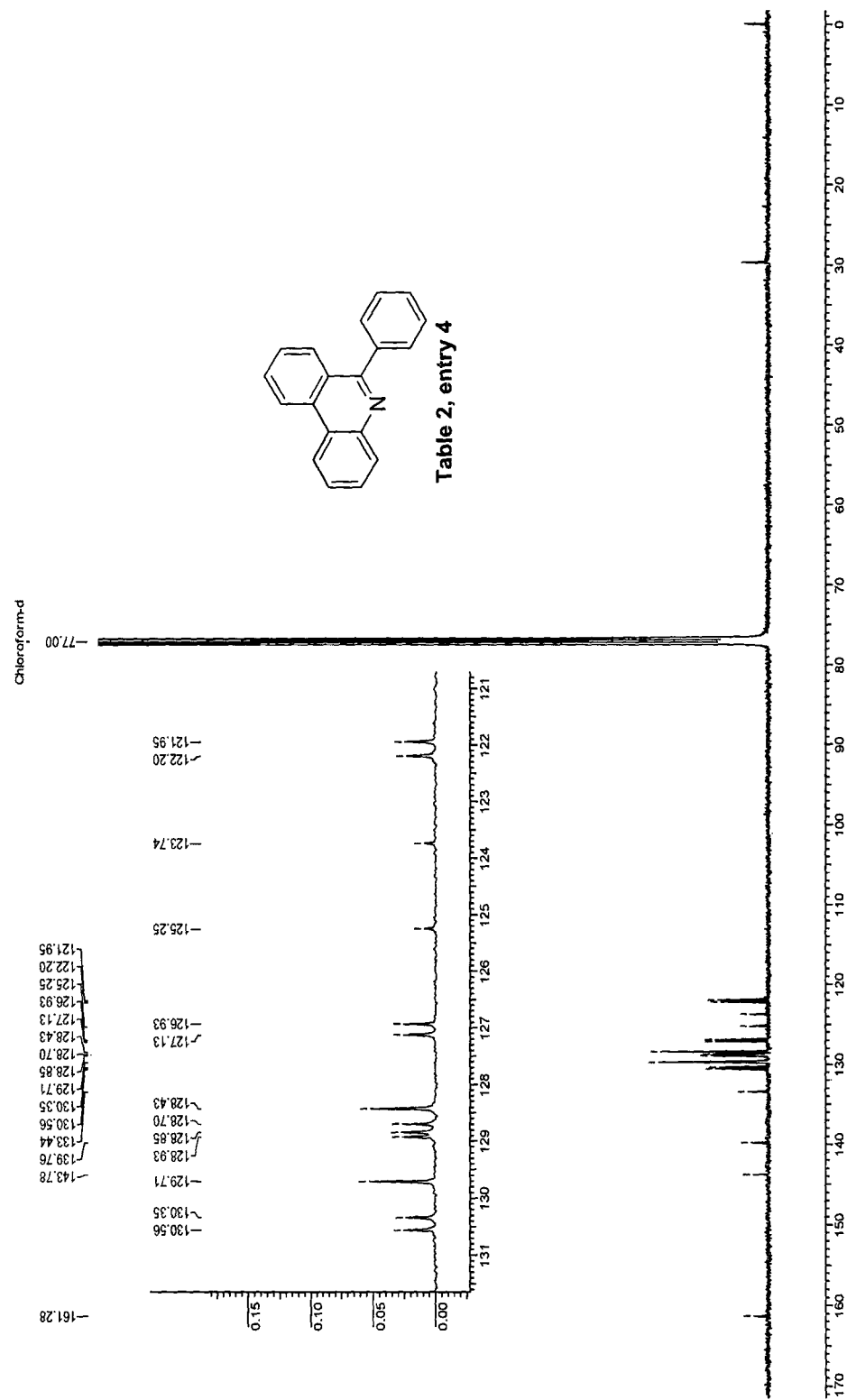
FIG. 14: $^{13}$C NMR spectra of compound of table 2, entry 4
Figure 15:
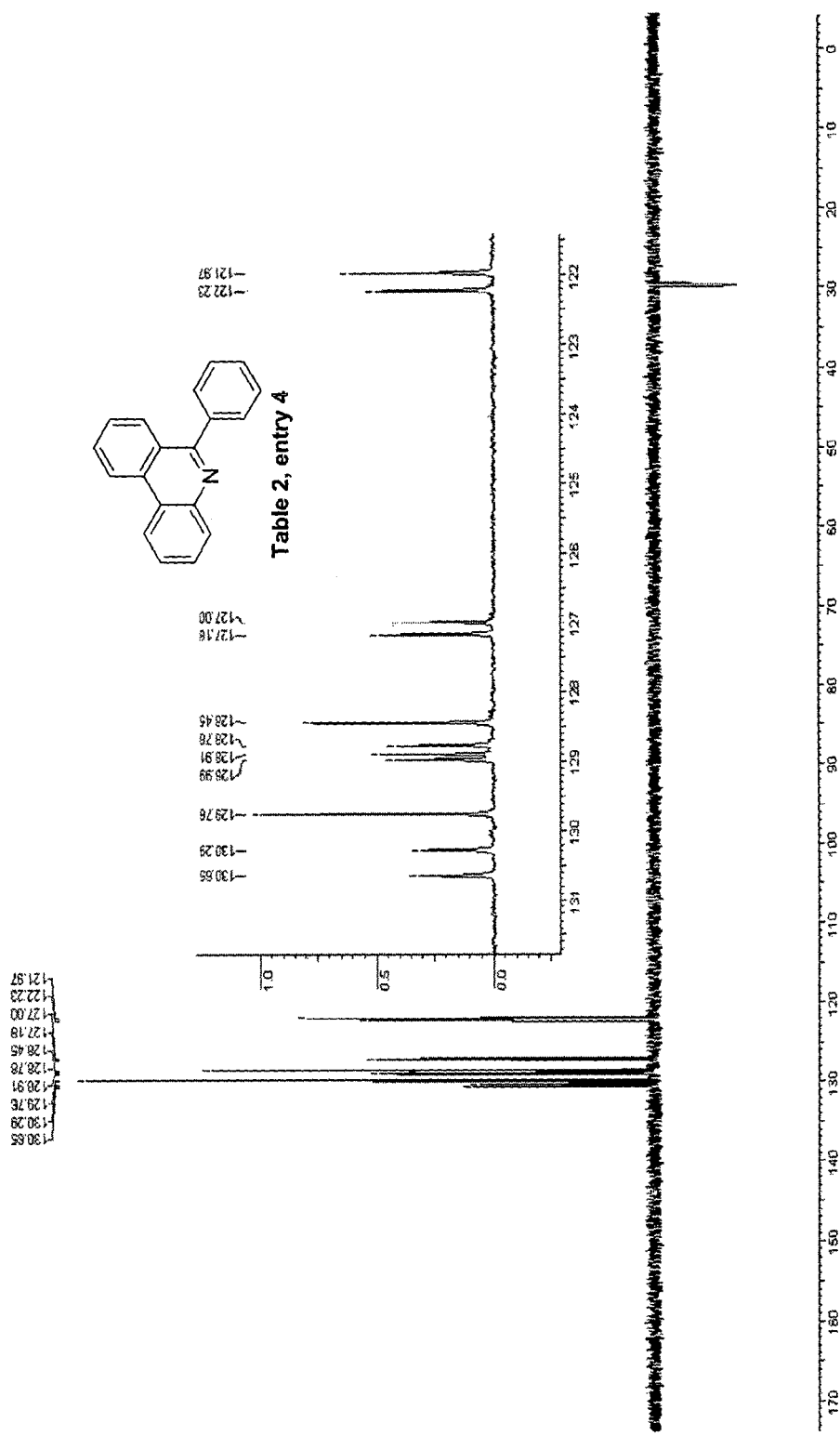
FIG. 15: DEPT NMR spectra of compound of table 2, entry 4
Figure 16:
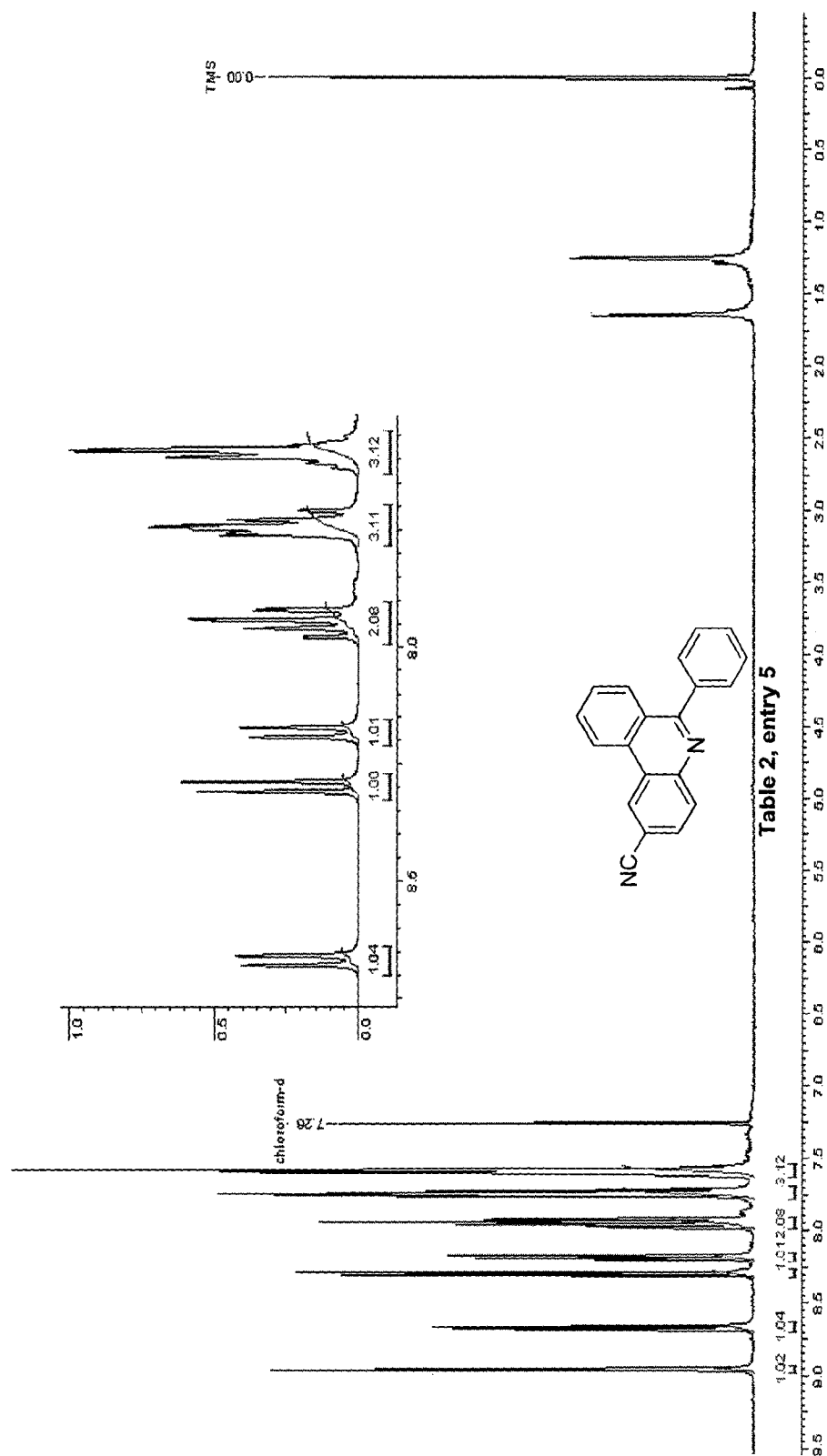
FIG. 16: $^1$H NMR spectra of compound of table 2, entry 5
Figure 17:
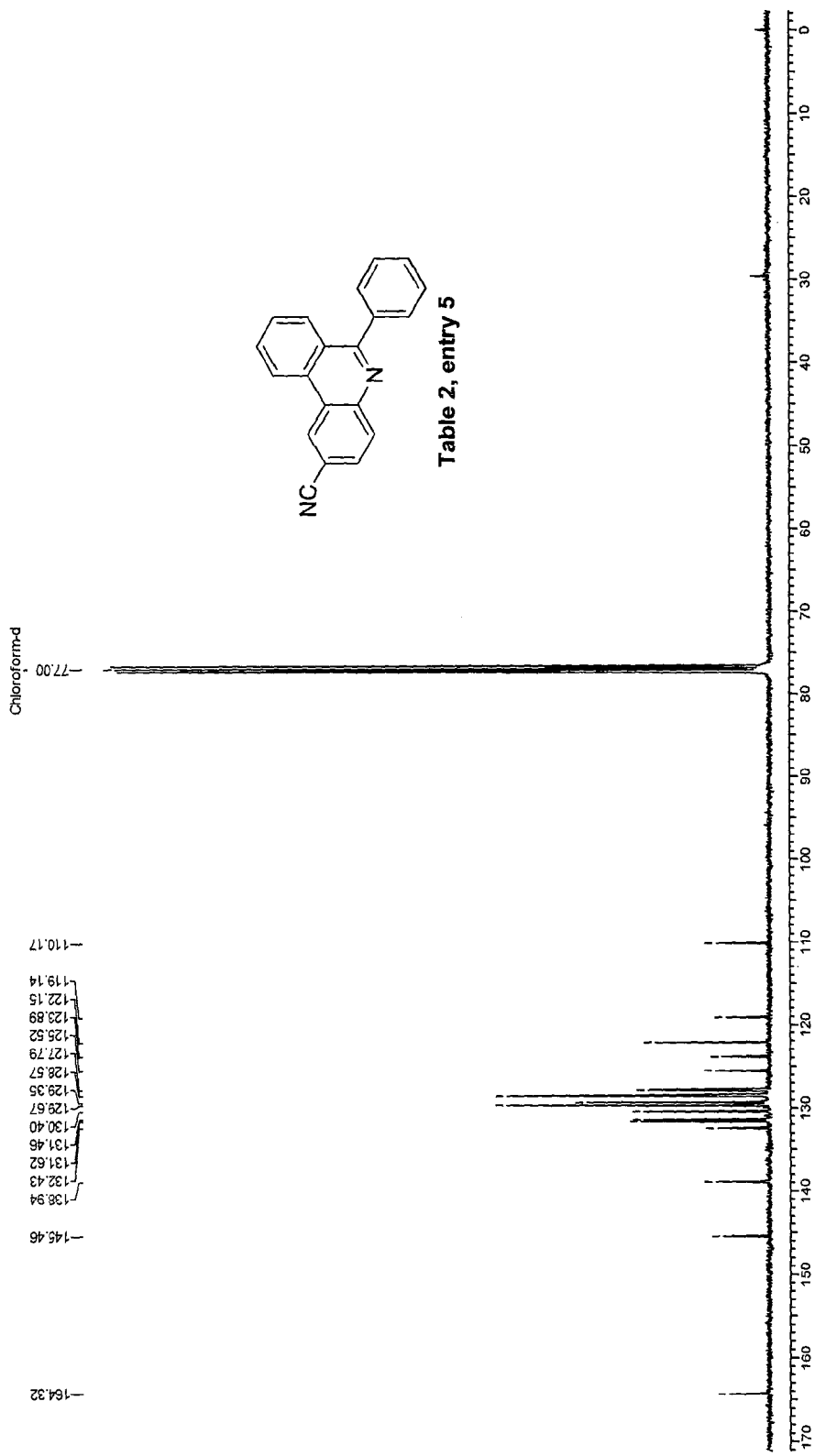
FIG. 17: $^{13}$C NMR spectra of compound of table 2, entry 5
Figure 18:
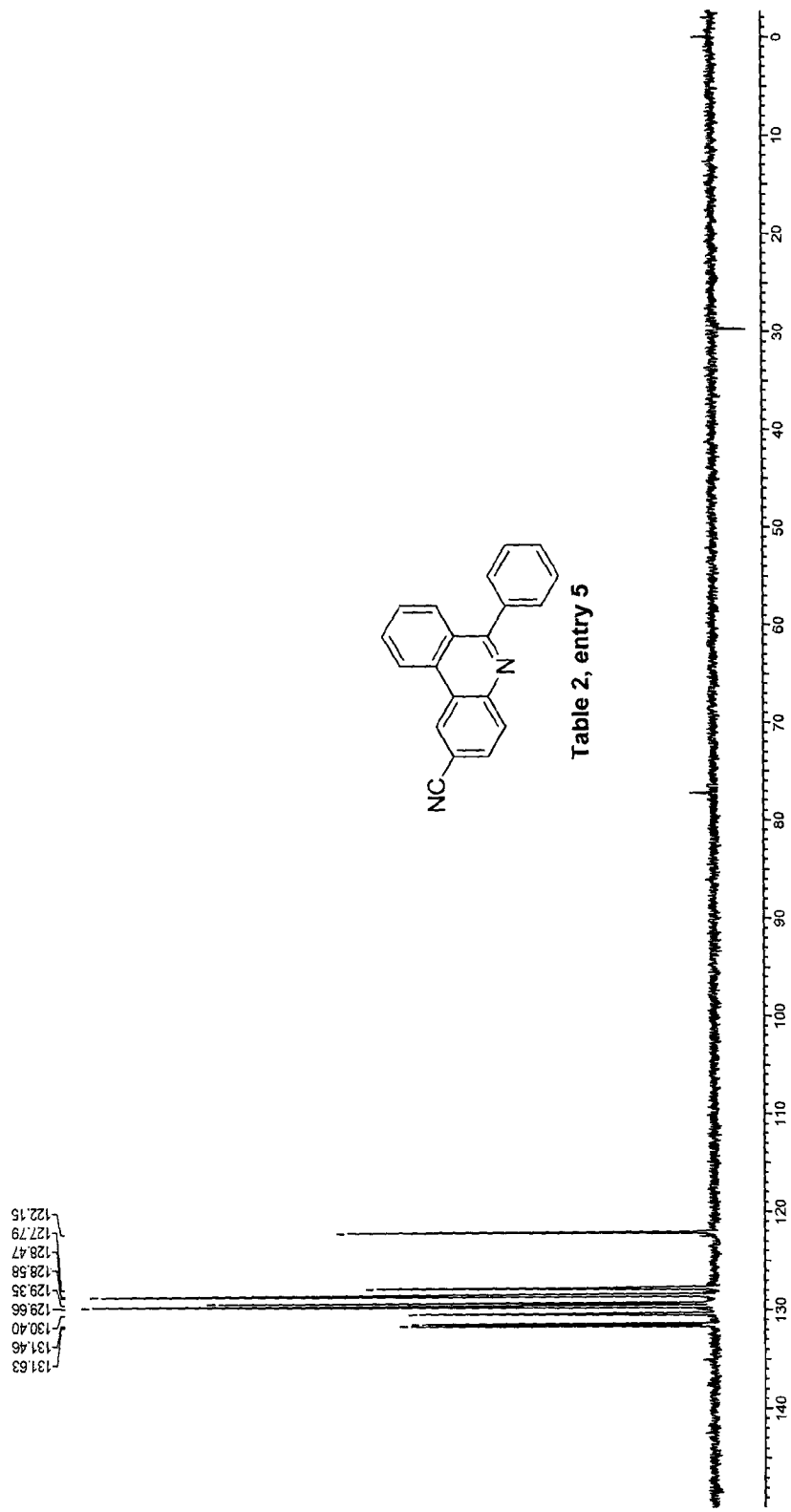
FIG. 18: DEPT NMR spectra of compound of table 2, entry 5
Figure 19:
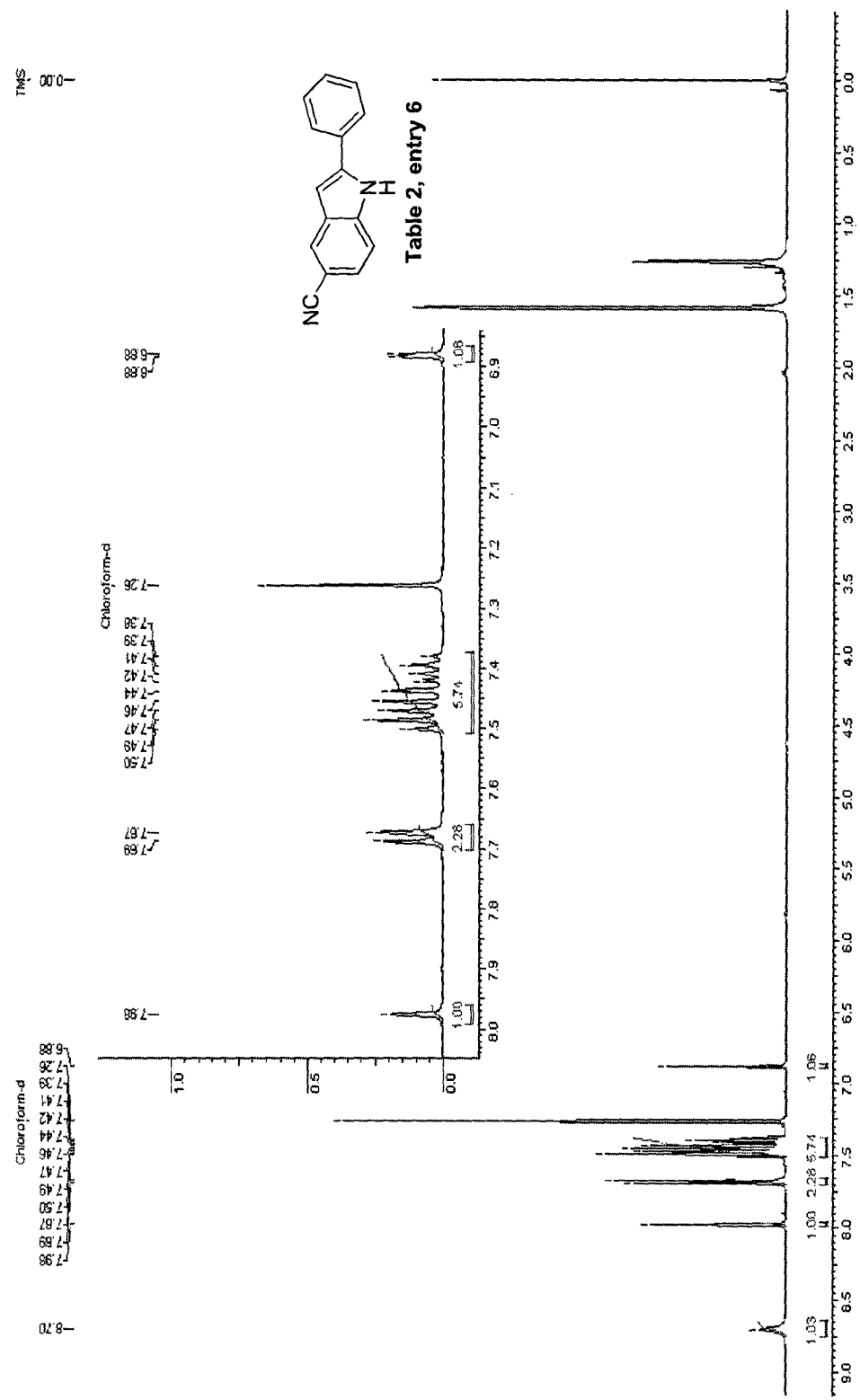
FIG. 19: $^1$H NMR spectra of compound of table 2, entry 6
Figure 20:
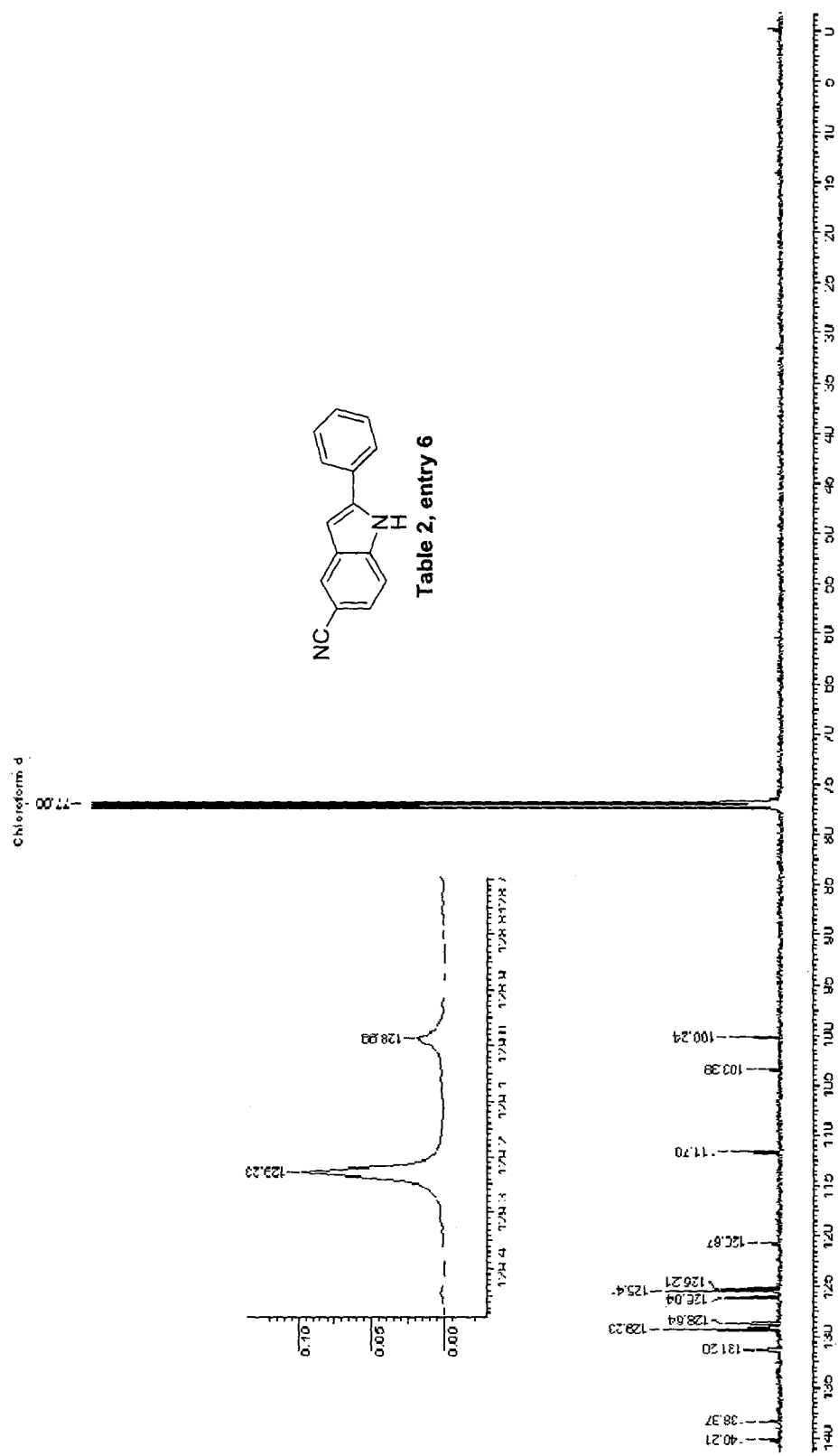
FIG. 20: $^{13}$C NMR spectra of compound of table 2, entry 6
Figure 21:
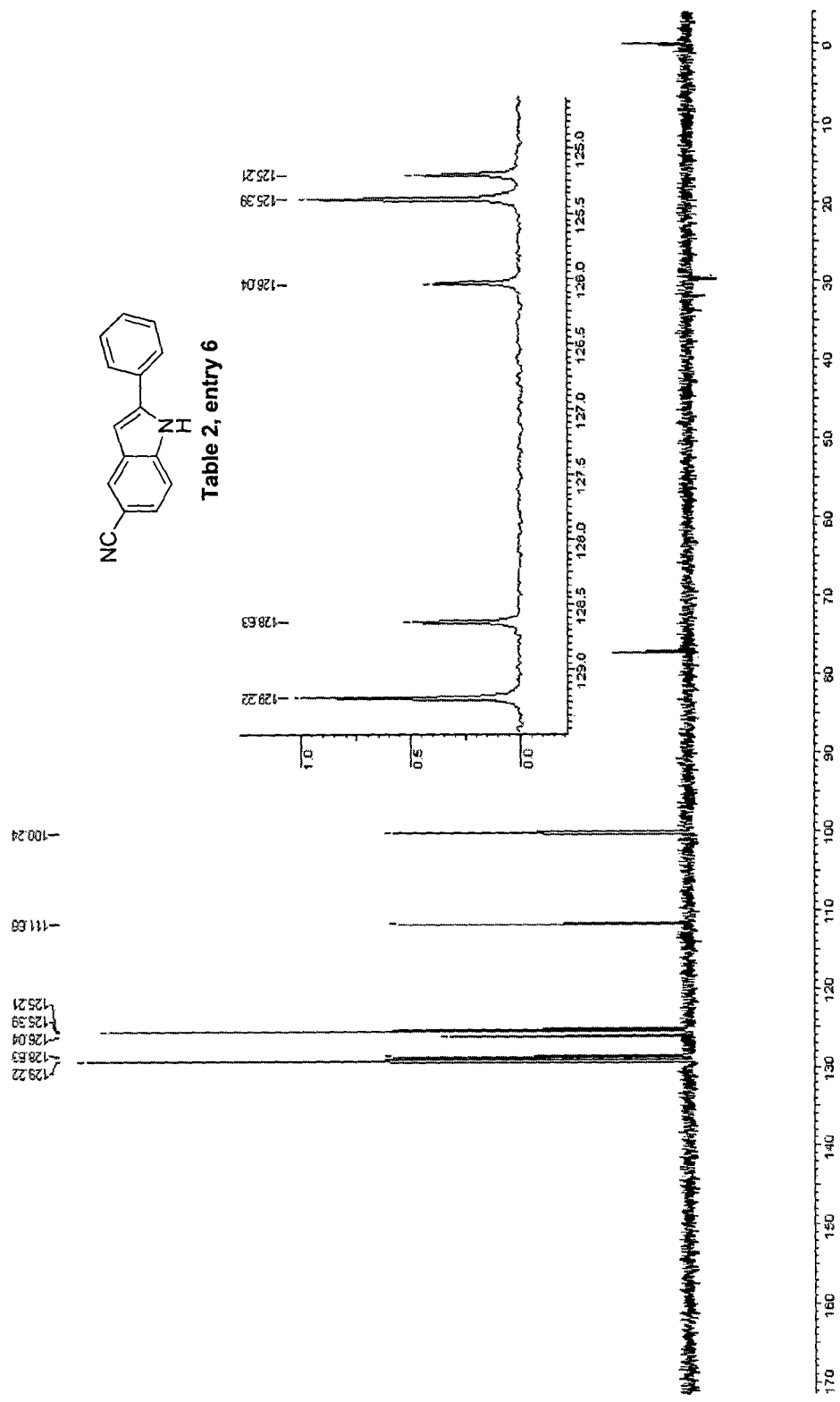
FIG. 21: DEPT NMR spectra of compound of table 2, entry 6

With the view to provide novel alternatives in anti malarial therapy, the present invention provides herein novel compounds and its analogues of general formula I, referred hereinafter as NCLite-M1 and its analogues.

The present invention provides the novel compounds and its analogues, positional isomers, stereoisomers, derivatives, and pharmaceutically acceptable salt thereof. of general formula I

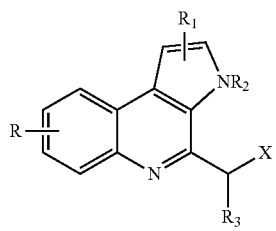

Formula I

Where R, $R_1$, $R_2$ are selected from H, halide, alkyl, aryl, hetero alkyl/aryl or heteroatom, X is selected from halide or activating groups such as OTf, OTs, B(OR)$_2$, SnR$_3$, SiR$_3$, and such like, and $R_3$ is selected from halide, purines or purine analogues or compound of formula III, wherein $R_4$ is selected from H, halide, alkyl, aryl, hetero alkyl/aryl, heteroatom.

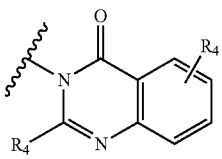

Formula III

In the present invention compound of formula I consists of NCLite-M1 and its intermediates and analogues as depicted herein.

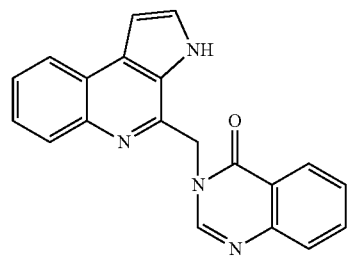 [SMILES: O=c1c2ccccc2ncn1Cc1nc2ccccc2c2cc[nH]c12]

NCLite-M1

Intermediate and its analogues

The present invention provides compound of formula II

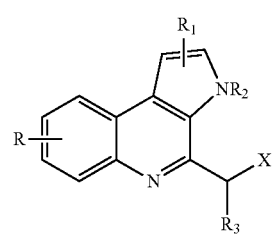

Formula II

R—$R_3$=H, halide, alkyl, aryl, hetero alkyl/aryl or heteroatom

X=halide or activating groups like OTf, OTs, B(OR)$_2$, SnR$_3$, SiR$_3$ and such like.

Further, $R_3$ may be selected from compound of Formula III and its analogues.

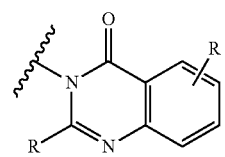

Formula III

The present invention provides a process for preparation of novel compounds of formula I beginning from compound 2,2-Iodo-N-(1-(1-(phenylsulfonyl)-1H-pyrrol-2-yl)ethylidene) aniline,

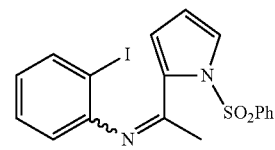

said process comprising:
a. refluxing a compound containing a carbonyl group selected from ketone or aldehyde and an aniline or a 2-halo aniline in dry solvent, particularly, toluene followed by work-up to obtain compound 2;
b. catalyzing the conversion of compound 2 of step (a) in the presence of Pd catalyst, ligand, base and solvent to obtain corresponding quinolone compound 3;
c. catalyzing the conversion of compound 3 of step (b) to obtain corresponding substituted quinoline of formula II;

d. treating quinazolin-4(3H)-one with product of step (c) in presence of $K_2CO_3$ at room temperature to obtain compound 7;

e. deprotecting the $SO_2Ph$ group of the compound 7 of step (d) by methanol —$K_2CO_3$ to obtain the desired product.

In an embodiment, the present invention provides a process for preparation of compounds of formula II, said process comprising:

a. refluxing a compound containing a carbonyl group selected from ketone or aldehyde and an aniline or a 2-halo aniline in dry seovlent, particularly, toluene followed by work-up to obtain compound 2;

b. catalyzing the conversion of compound 2 of step (a) in the presence of Pd catalyst, ligand, base and solvent to obtain corresponding quinolone compound 3;

c. catalyzing the conversion of compound 3 of step (b) to obtain corresponding substituted quinoline of formula II;

d. synthesizing Marinoquinoline compounds from product of step (b) by refluxing with potassium terbutoxide or methanol-$K_2CO_3$ at room temperature;

e. synthesizing Aplidiopsamine A from Marinoquinoline A analogue formed in step (c) by treatment with adenine and further deprotecting the $SO_2Ph$ group by methanol and $K_2CO_3$.

The process for the preparation of compound I & II is depicted in Scheme 1.

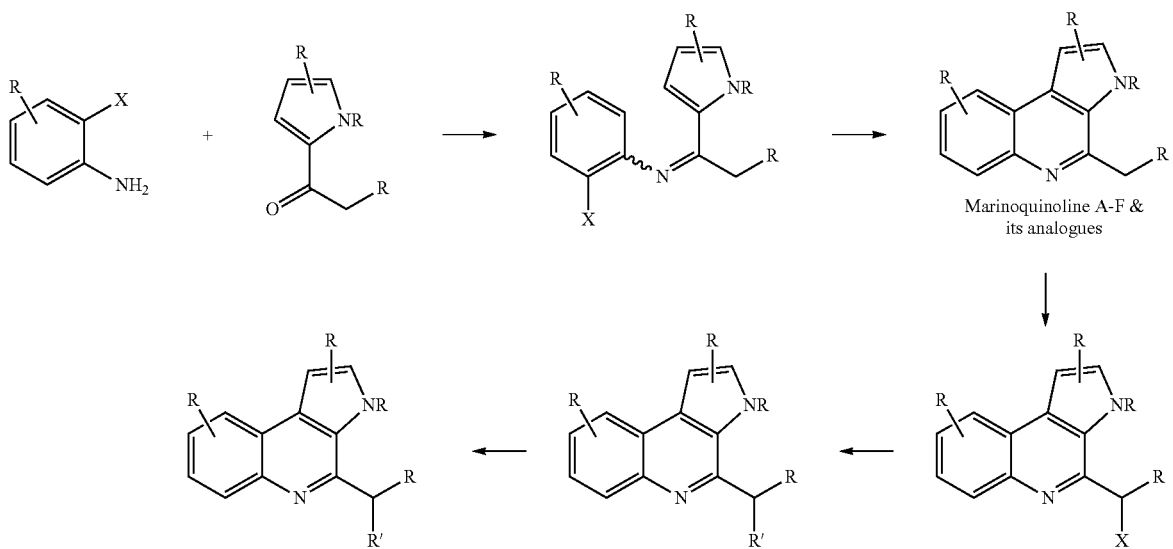

Scheme 1

Where,
R, R' = maximum no. of substitutents possible, which inculdes H, halides, alkyl, aryl, heteroalkyl/aryl
X = any halide, activating groups like, OTf, OTs, B(OR)$_2$, SnR$_3$, SiR$_3$ In a preferred embodiment of the process of preparation of compound of formula II is depicted below in Scheme 2 which leads to the formation of Aplidiopsamine A and Marinoquinoline A.

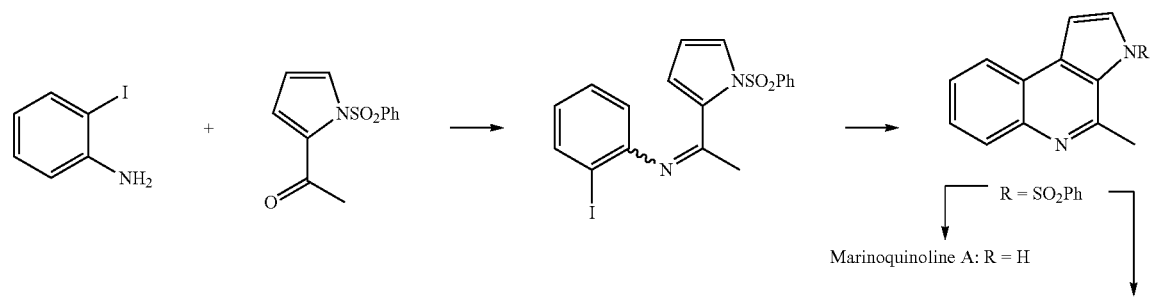

Scheme 2

Marinoquinoline A: R = H

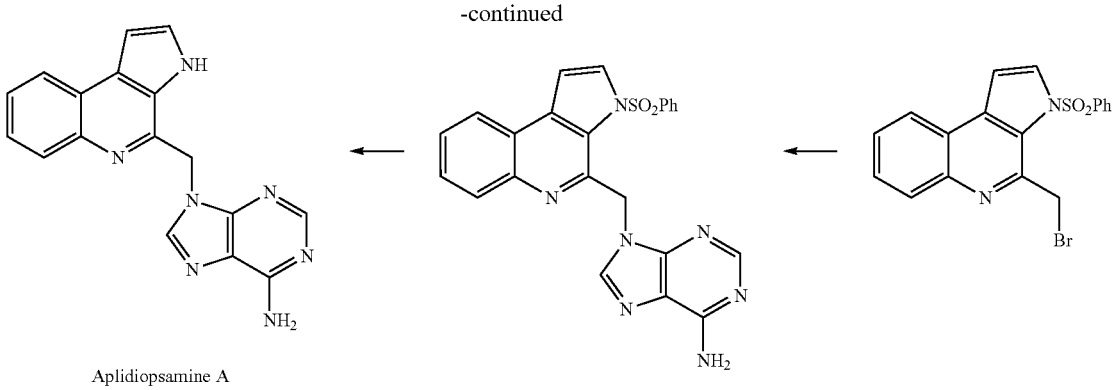

Aplidiopsamine A

In another preferred aspect of the invention, the process of Scheme 1 which leads to formation of NCLite-M1 is depicted below in the Scheme 3.

Scheme 3

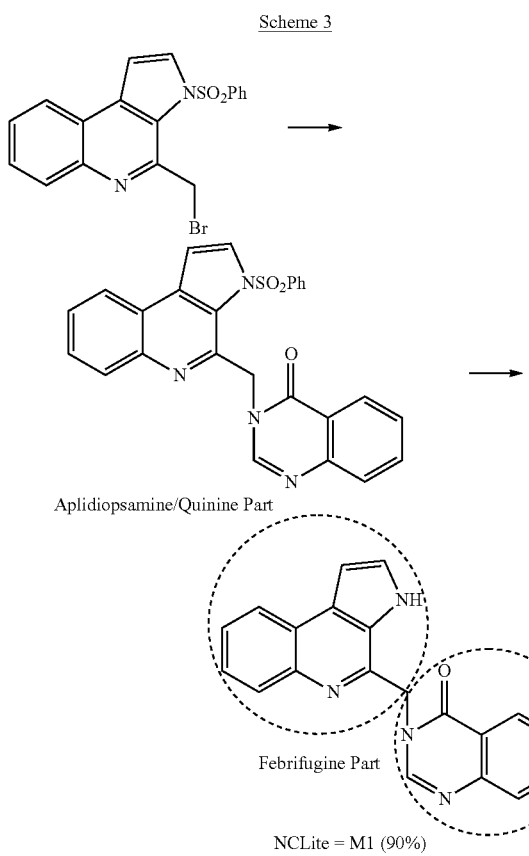

Aplidiopsamine/Quinine Part

Febrifugine Part

NCLite = M1 (90%)

In an aspect of invention, the yield of compound of formula I may be in the range of 25% to 98%.

In an aspect of invention, the yield of compound of formula II may be in the range of 40% to 98%.

In a preferred embodiment, the Pd catalyst used in the process above is $Pd(OAc)_2$ in the range of 1 mol % to 20 mol %.

In a preferred embodiment, the ligand used in the process above is selected from $PPh_3$, Neocuproine, and $PCy3$ in the range of 1 mol % to 40 mol %, and is preferably $PPh_3$ in the range of 1 mol % to 40 mol %.

In a preferred embodiment, the base used in the process above is selected from $K_2CO_3$, $Cs_2CO_3$, $Ag_2CO_3$, KOtBu in the range of 1 mol % to 200 mol %, and is preferably $Ag_2CO_3$ in the range of 1 mol % to 200 mol %.

In a preferred embodiment, the solvent used in the process above is chosen from 1,4 dioxane, dimethyl formamide, DMF, Benzene, tetra hydro furan THF and is preferably 1,4 dioxane.

In a preferred embodiment, the catalyst for the process of step (c) is NBS and radical initiator like AIBN, ABCN and is preferably BPO catalyzed NBS.

In an aspect of the invention, the compound of formula I & II may possess activity against other known or unknown pathogens and are useful in treating a subject in need of a treatment against such pathogens.

In a preferred embodiment, the compound NCLite-M1 was tested for anti-malarial activity against a known parasite *Plasmodium falciprum* 3D7 was used, which is chloroquine sensitive strain and the results are tabulated herein.

In another preferred embodiment, the compound of formula I are useful as anti mycobacterial agents, Compound formula I may be used for treatment of infections caused by Mycobacteria in subjects in the need of the same. Brent Copp et al in Natural product growth inhibitors of *Mycobacterium tuberculosis*, Nat. Prod. Rep., 2007, 24, 278-297 discusses the anti mycobacterial activity and anti tumour of compounds 225-23, which are alkaloids isolated from various natural sources.

In another embodiment, a pharmaceutical composition is provided comprising a compound of formula (I & II), or a stereoisomer, or ester or pharmaceutically acceptable salt thereof, and a pharmaceutically acceptable carrier, diluent or excipient.

The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, injections, gels and microspheres, In another embodiment, the present invention relates to administering 'an effective amount' of the 'composition of invention' to the subject suffering from said disease. Accordingly, compound of formula I and pharmaceutical compositions containing them may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

Pharmaceutical compositions of the invention are formulated so as to allow the active ingredients contained therein to be bioavailable upon administration of the composition to a patient. Compositions that will be administered to a subject or patient may take the form of one or more dosage units. The dosage forms can also be prepared as sustained, controlled, modified and immediate dosage forms.

The following examples are given by way of illustration and therefore should not be construed to limit the scope of the present invention in any manner.

EXAMPLES

Example 1

1-(1-(methylsulfonyl)-1H-pyrrol-2-yl)ethanone (1)

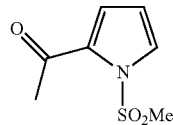

Procedure:

To a solution of acetic anhydride (1.3 mL, 0.13 mmol) in 5 mL of 1,2-dichloroethane at 25° C. was added $BF_3$—$OEt_2$ (3.4 mL, 0.27 mmol). The mixture was stirred for 10 min, a solution of methylsulfonyl protected pyrrole (500 mg, 0.61 mmol) in 2 mL of 1,2-dichloroethane was added, and the mixture was stirred at 25° C. for 90 min. The reaction was quenched with cold water, and the reaction products were extracted into dichloromethane. The residue remaining after concentration at reduced pressure was chromatographed in a column of silica gel (70-230 mesh), eluting with ethyl acetate-petroleum ether (1:9) to afford 1-(1-(methylsulfonyl)-1H-pyrrol-2-yl)ethanone (440 mg, 68%).

$R_f$=0.50 (4:1 PE:EtOAc); MP 62-64° C.; IR(Nujol): $v_{max}$ 2925, 2854, 1711, 1679, 1539, 1459, 1375, 938, 847, 768 cm$^{-1}$; $^1$H NMR (500 MHz, CDCl$_3$): δ 2.49 (s, 3H), 3.72 (s, 3H), 6.28 (t, J=3.7 Hz, 1H), 7.11 (dd, J=1.7, 3.7 Hz, 1H), 7.56 (dd, J=1.8, 3.2 Hz, 1H); $^{13}$C NMR (125 MHz, CDCl$_3$): δ 27.2, 43.1, 110.1, 124.8, 129.9, 133.2, 187.3; HRMS-ESI (m/z); calcd for $[C_7H_9O_3NS+H]^+$, 188.0376. found 188.0379.

Example 2

2-Iodo-N-(1-(1-(phenylsulfonyl)-1H-pyrrol-2-yl)ethylidene) aniline (2)

Procedure:

To a dry two

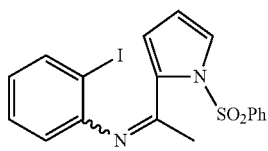

neck round bottom flask, equipped with Dean-Stark apparatus, containing freshly activated 4 Å molecular sieves, ketone 1 (100 mg, 0.40 mmol), Iodoaniline (439 mg, 2.00 mmol) and p-toluenesulphonic acid (8 mg, 0.04 mmol), was added dry toluene under argon atmosphere and the reaction mixture was refluxed for 18 h. It was then cooled to room temperature and filtered. The filtrate was evaporated under reduced pressure. Ethyl acetate was added and the organic layer was washed with saturated sodium bicarbonate solution, brine and dried over sodium sulphate. Evaporation of ethyl acetate followed by silica gel chromatography (49:1 PE:EtOAc) furnished 2 as yellow solid (145 mg, 80%).

$R_f$=0.50 (19:1 PE:EtOAc); MP 145-147° C.; IR(Nujol): $v_{max}$ 2928, 2851, 1456, 1374, 721 cm$^{-1}$; $^1$H NMR (400 MHz, Acetone-D$_6$): δ2.03 (s, 3H), 6.49 (t, J=3.1 Hz, 1H), 6.70 (dd, J=1.5, 7.8 Hz, 1H), 6.85 (ddd, J=1.5, 7.8 Hz, 1H), 7.03 (dd, J=1.8, 3.7 Hz, 1H), 7.36-7.48 (m, 3H), 7.63 (t, J=7.5 Hz, 1H), 7.75-7.81 (m, 4H); $^{13}$C NMR (100 MHz, Acetone-D$_6$): δ 19.5, 89.1, 111.9, 119.6, 120.5, 125.6, 127.8, 129.0, 129.6, 129.8, 134.1, 135.7, 139.5, 141.4, 152.3, 158.5; HRMS-ESI (m/z): calcd for $[C_{18}H_{15}O_2N_2IS+H]^+$, 450.9972. found 450.9960.

Example 3

4-Methyl-3-(phenylsulfonyl)-3H-pyrrolo[2,3-c]quinoline (3)

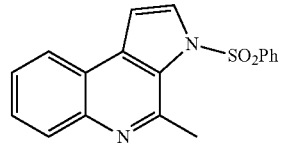

Procedure A (in Round Bottom Flask with Reflux Condenser):

To a two neck round bottom flask, equipped a with a water condenser, was added Pd(OAc)$_2$ (2 mg, 0.01 mmol), PPh$_3$ (6 mg, 0.02 mmol) and Ag$_2$CO$_3$ (61 mg, 0.22 mmol). To this was added solution of 2 (50 mg, 0.11 mmol) in 1,4-dioxane (1 ml) by means of a syringe and the reaction mixture was refluxed for 2 h. After cooling to room temperature the reaction mixture was filtered through celite and 1,4-dioxane was evaporated. The residue was dissolved in ethyl acetate. The organic layer was washed with brine and dried over sodium sulphate. After evaporation of the solvent, the crude product was purified by using column chromatography on silica gel (4:1 PE:EtOAc) to yield 3 as a brown solid (32 mg, 91%).

Procedure B (in Sealed Tube):

To a sealed tube containing magnetic stirring bar was added Pd(OAc)$_2$ (1 mg, 2 mol %), PPh$_3$ (2 mg, 4 mol %) and Ag$_2$CO$_3$ (24 mg, 0.09 mmol). To this was added solution of 2 (100 mg, 0.22 mmol) in 1,4-dioxane (1 ml) by means of a syringe and the tube was sealed and heated at 120° C. for 10 h. After cooling to room temperature the reaction mixture was filtered through celite and 1,4-dioxane was evaporated. The residue was dissolved in ethyl acetate. The organic layer was washed with brine and dried over sodium sulphate. After evaporation of the solvent, the crude product was purified by using column chromatography on silica gel (4:1 PE:EtOAc) to yield 3 as a brown solid (67 mg, 93%).

$R_f$=0.50 (7:3 PE:EtOAc); MP 143-145° C.; IR(CHCl$_3$): $v_{max}$ 3148, 3060, 2928, 2851, 1618, 1577, 1366, 1176, 990, 751, 685, 592 cm$^{-1}$; $^1$H NMR (500 MHz, CDCl$_3$): δ 2.90 (s, 3H), 7.22 (d, J=3.7 Hz, 1H), 7.43 (t, J=7.9 Hz, 2H), 7.54 (q, J=7.0 Hz, 2H), 7.62 (m, 1H), 7.68 (d, J=7.3 Hz, 2H), 8.02 (d, J=8.2 Hz, 114), 8.05-8.09 (m, 2H); $^{13}$C NMR (125 MHz, CDCl$_3$): δ 26.1, 105.6, 121.5, 122.8, 126.1, 126.4, 128.0, 128.53, 128.55, 129.5, 131.8, 134.1, 134.7, 139.3, 143.3, 146.7; HRMS-ESI (m/z): calcd for $[C_{18}H_{14}O_2N_2S+H]^+$, 323.0849. found 323.0839.

Example 4

Marinoquinoline A

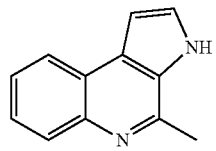

Procedure:

To the solution of 3 (50 mg, 0.15 mmol) in MeOH (2 ml) was added $K_2CO_3$ (42 mg, 0.31 mmol). The reaction mixture was refluxed for 1 h. Then it was quenched with water and extracted with ethyl acetate. The organic layer was washed with brine and dried over sodium sulphate. After evaporation of the solvent, the crude product was purified by using silica gel column chromatography (1:1 PE:EtOAc) to obtain Marinoquinoline A as a white solid (27 mg, 96%).

$R_f$=0.30 (1:1 PE:EtOAc); MP 237-239° C.; IR(Nujol): $\nu_{max}$ 3379, 2917, 2857, 1465, 1451, 1377, 751 cm$^{-1}$; $^1$H NMR (500 MHz, Acetone-D$_6$): δ 2.87 (s, 3H), 7.15 (d, J=2.8 Hz, 1H), 7.50-7.57 (m, 2H), 7.62 (d, J=2.7 Hz, 1H), 8.05 (dd, J=2.1, 7.3 Hz 1H), 8.25 (dd, J=2.1, 7.3 Hz, 1H), 11.29 (br s, 1H); $^{13}$C NMR (125 MHz, Acetone-D$_6$): δ 21.0, 101.9, 123.7, 124.1, 125.7, 126.1, 127.4, 128.5, 129.5, 129.7, 143.3, 146.8; HRMS-ESI (m/z): calcd for $[C_{12}H_{10}N_2+H]^+$, 183.0917. found 183.0914.

Example 5

4-(Bromomethyl)-3-(phenylsulfonyl)-3H-pyrrolo[2,3-c]quinoline (4)

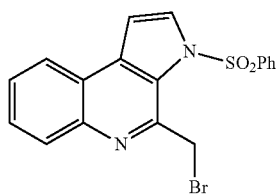

Procedure:

To the solution of 3 (60 mg, 0.18 mmol) in dry carbon tetrachloride (3 ml) was added NBS (132 mg, 0.74 mmol) and radical initiator benzoyl peroxide (9 mg, 0.03 mmol). The reaction mixture was refluxed for an 8 h and then cooled to room temperature. The precipitated solid was filtered of and the filtrate was concentrated. Crude product was rapidly passed through silica gel column (7:1.5 PE:EtOAc) to obtain 4 (56 mg, 75%). The purity of the obtained product was more than 90% and it was used for further reaction as soon as possible to avoid decomposition.

$R_f$=0.60 (7:3 PE:EtOAc); IR (Nujol): $\nu_{max}$ 2923, 2862, 1459, 1374, 1185, 1083, 727, 587 cm$^{-1}$; $^1$H NMR (400 MHz, CDCl$_3$): δ 5.30 (s, 2H), 7.28 (d, J=3.4 Hz, 1H), 7.44 (t, J=7.6 Hz, 2H), 7.54 (d, J=7.5 Hz, 1H), 7.61 (d, J=8.3 Hz, 1H), 7.65-7.71 (m, 1H), 7.75 (d, J=8.3 Hz, 2H), 8.06 (d, J=3.8 Hz, 1H), 8.10 (t, J=8.5 Hz, 2H); $^{13}$C NMR (100 MHz, CDCl$_3$): δ 33.9, 106.9, 122.1, 122.9, 126.6, 127.4, 128.6, 129.3, 129.6, 129.8, 132.9, 134.3, 136.6, 138.1, 143.5, 144.9; HRMS-ESI (m/z): calcd for $[C_{18}H_{13}O_2N_2SBr(79)+H]^+$, 400.9959. found 400.9942 and $[C_{18}H_{13}O_2N_2SBr(81)+H]^+$, 402.9939. found 402.9917.

Example 6

4-(((6-Chloro-9H-purin-9-yl)methyl)-3-(phenylsulfonyl)-3H-pyrrolo[2,3-c]quinoline (5)

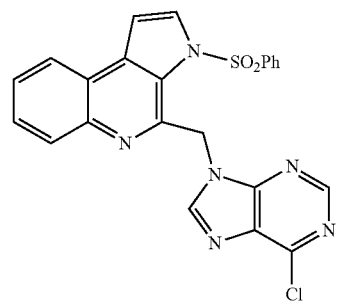

Procedure:

A two neck dry round bottom flask containing 6-chloropurine (38 mg, 0.24 mmol), $K_2CO_3$ (43 mg, 0.31 mmol) and dry DMF (0.5 ml) was stirred at 50° C. under argon atmosphere for 1 h. It was then cooled to room temperature and to the reaction mixture was added a solution of 4 (50 mg, 0.12 mmol) in dry DMF (0.5 ml). The reaction mixture was heated to 50° C. and stirred at the same temperature for 6 h. The reaction mixture was cooled to room temperature and quenched with ice cold water and extracted with ethyl acetate. The organic layer was washed with brine and dried over sodium sulphate. After evaporation of the solvent the crude compound was purified using silica gel column chromatography (4:1 PE:EtOAc) to yield 5 as off white solid (42 mg, 70%).

$R_f$=0.40 (3:2 PE:EtOAc); MP 223-225° C.; IR(Nujol): $\nu_{max}$ 2923, 1462, 1376, 1176, 727 cm$^{-1}$; $^1$H NMR (500 MHz, CDCl$_3$): δ 6.17 (s, 2H), 7.31 (d, J=3.7 Hz, 1H), 7.52 (t, J=7.9 Hz, 2H), 7.54-7.58 (m, 2H), 7.64 (t, J=7.3 Hz, 1H), 7.70-7.74 (m, 1H), 7.82 (d, J=7.6 Hz, 2H), 8.05 (d, J=3.7 Hz, 1H), 8.06-8.09 (m, 1H), 8.31 (s, 1H), 8.58 (s, 1H); $^{13}$C NMR (125 MHz, CDCl$_3$): δ 47.9, 107.2, 121.9, 122.8, 126.4, 126.5, 127.4, 128.5, 129.5, 129.9, 131.2, 132.3, 134.6, 136.2, 138.4, 141.1, 142.8, 147.6, 150.5, 151.7, 152.5; HRMS-ESI (m/z): calcd for $[C_{23}H_{15}O_2N_6ClS+H]^+$, 475.0738. found 475.0727.

Example 7

Aplidiopsamine A (6)

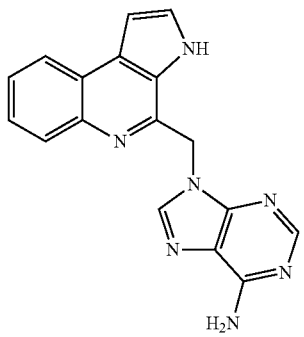 [SMILES: Nc1ncnc2c1ncn2Cc1nc2ccccc2c2cc[nH]c12]

Procedure:

To a dry sealed tube containing 5 (20 mg, 0.04 mmol) was added saturated methanolic ammonia solution (5 ml). The tube was sealed with Teflon cap and the reaction mixture was refluxed at 150° C. for 24 h. After cooling to room temperature ammonia was allowed to escape and methanol was evaporated. The crude product was purified using column chromatography on silica gel (49:1 DCM:MeOH) to yield Aplidiopsamine A as a off white solid (9 mg, 69%).

$R_f$=0.40 (19:1 DCM:MeOH); MP 229-231° C.; IR(Nujol): $v_{max}$ 3351, 2923, 1684, 1462, 1374, 1116, 1152, 735, 716 cm$^{-1}$; $^1$H NMR (400 MHz, DMSO-D$_6$): δ 5.94 (s, 2H), 7.20 (s, 1H), 7.25 (br s, 2H), 7.43-7.55 (m, 2H), 7.75 (d, J=7.8 Hz, 2H), 8.07 (s, 1H), 8.26 (d, J=7.8, 1H), 8.33 (s, 1H), 12.39 (br s, 1H); $^{13}$C NMR (100 MHz, DMSO-D$_6$): δ 44.8, 101.6, 118.7, 123.4, 125.9, 126.9 (2C), 128.2, 128.4, 129.2 (2C), 141.7, 142.5, 143.6, 150.1, 152.7, 156.2; HRMS-ESI (m/z): calcd for [C$_{17}$H$_{13}$N$_7$+H]$^+$, 316.1305. found 316.1304.

Example 8

3-((3-(Phenylsulfonyl)-3H-pyrrolo[2,3-c]quinolin-4yl)methyl)quinazolin-4(3H)-one (7)

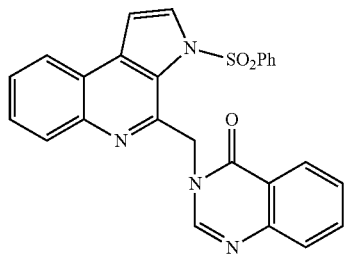

Procedure:

To a two neck dry round bottom flask was added 6 (50 mg, 0.34 mmol), K$_2$CO$_3$ (60 mg, 0.43 mmol) and dry DMF (0.5 ml) under argon atmosphere. The reaction mixture was stirred at 50° C. for 1 h, then cooled to room temperature followed by addition of a solution of 4 (70 mg, 0.17 mmol) in dry DMF (0.5 ml). It was heated to 50° C. and stirred at same temp for 6 h. The reaction mixture was cooled to room temperature and quenched with ice cold water and extracted with ethyl acetate. The organic layer was washed with brine and dried over sodium sulphate. After evaporation of the solvent, the crude compound was purified using silica gel column chromatography (7:3 PE:EtOAc) to yield 7 as a white solid (60 mg, 73%).

$R_f$=0.50 (1:1 PE:EtOAc); MP 201-203° C.; IR(Nujol): $v_{max}$ 2925, 2854, 1675, 1612, 1461, 1376, 1176, 726, cm$^{-1}$; $^1$H NMR (500 MHz, CDCl$_3$): δ 5.85 (s, 2H), 7.26 (d, J=3.8 Hz, 1H), 7.43-7.55 (m, 5H), 7.60 (t, J=7.3 Hz, 1H), 7.72-7.79 (m, 3H), 7.85 (d, J=7.3 Hz, 2H), 8.00 (d, J=3.8 Hz, 1H), 8.01-8.05 (m, 1H), 8.11 (s, 1H), 8.23 (d, J=7.6 Hz, 1H); $^{13}$C NMR (125 MHz, CDCl$_3$): δ 49.9, 107.1, 121.9, 122.3, 122.6, 126.5, 126.8, 126.9, 127.4, 128.1, 129.7, 129.8, 131.9, 134.0, 134.5, 135.8, 138.4, 142.2, 142.9, 148.4, 161.3; HRMS-ESI (m/z): calcd for [C$_{26}$H$_{18}$O$_3$N$_4$S+Na]$^+$, 489.0992. found 489.0980.

Example 9

NCLite-M1 (8)

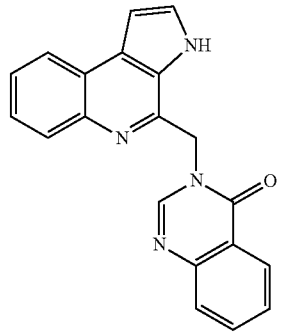 [SMILES: O=c1c2ccccc2ncn1Cc1nc2ccccc2c2cc[nH]c12]

3-((3H-pyrrolo[2,3-c]quinolin-4-yl)methyl)quinazolin-4(3H)-one

Procedure:

To a two neck round bottom flask was added 7 (20 mg, 0.04 mmol), K$_2$CO$_3$ (17 mg, 0.12 mmol) and methanol (1 ml). The reaction mixture was refluxed for 1 h, brought to room temperature and quenched with water. Extraction with dichloromethane, drying over sodium sulphate and evaporation gave the crude compound, which was purified using column chromatography on silica gel (1:1 PE: EtOAc) to yield NCLite-M1 as white solid (12 mg, 90%).

$R_f$=0.30 (1:1 PE:EtOAc); MP 211-213° C.; IR(Nujol): $v_{max}$ 3286, 2925, 2855, 1668, 1614, 1464, 1375, 766, 739 cm$^{-1}$; $^1$H NMR (400 MHz, DMSO-D$_6$): δ 5.78 (s, 2H), 7.20 (t, J=2.5 Hz, 1H), 7.43 (t, J=8.3, 1H), 7.48-7.58 (m, 2H), 7.70 (d, J=8.3, 1H), 7.74-7.80 (m, 2H), 7.88 (t, J=8.5, 1H), 8.12 (d, J=7.8 Hz, 1H), 8.27 (d, J=7.8 Hz, 1H), 8.6 (s, 1H), 12.39 (br s, 1H); $^{13}$C NMR (100 MHz, DMSO-D$_6$): 47.1, 101.5, 121.87, 121.94, 123.3, 125.7, 125.8, 126.4, 126.9, 127.2, 127.5, 127.9, 128.2, 129.1, 134.7, 141.6, 143.7, 148.5, 149.6, 160.5; HRMS-ESI (m/z): calcd for [C$_{20}$H$_{14}$ON$_4$+H]$^+$, 327.1240. found 327.1231.

Example 10

General Procedure for Imine Formation and Cyclization (Table 2, Entry 1-6)

To a dry two neck round bottom flask, equipped with Dean-Stark apparatus, containing freshly activated 4 Å molecular sieves, ketone (1.2 equiv.), Iodoaniline (1 equiv.) and p-toluenesulphonic acid (0.1 equiv.), was added dry toluene under argon atmosphere and the reaction mixture was refluxed for 12-24 h. It was then cooled to room temperature and filtered. The filtrate was evaporated under reduced pressure. Ethyl acetate was added and the organic layer was washed with saturated sodium bicarbonate solution, brine and dried over sodium sulphate. Evaporation of ethyl acetate provided crude imine, which was used further without any purification.

To a sealed tube containing magnetic stirring bar was added Pd(OAc)$_2$ (0.02 equiv.), PPh$_3$ (0.04 equiv.) and Ag$_2$CO$_3$ (0.4 equiv.). To this was added solution of crude imine (1 equiv.) in 1,4-dioxane by means of a syringe and the tube was sealed and heated at 120° C. for 8-24 h. After cooling to room temperature the reaction mixture was filtered through celite and 1,4-dioxane was evaporated. The residue was dissolved in ethyl acetate. The organic layer was washed with brine and dried over sodium sulphate. After evaporation of the solvent, the crude product was purified by using column chromatography on silica gel (PE:EtOAc) to yield cyclized product in 51-90% yield over two steps.

TABLE 1

Optimization studies on cyclization of iodo-imine 2 to pyrroloquinoline 3.

$$2 \xrightarrow{\text{Pd(OAc)}_2, \text{ ligand, base, solvent}} 3$$

| entry | catalyst (equiv) | ligand (equiv) | base (equiv) | solvent | temp | time | yield |
|---|---|---|---|---|---|---|---|
| 01 | — | Neocuproine (0.50) | KOtBu (2.5) | Benzene | 100° C. | 18 h | trace |
| 02 | Pd(OAc)$_2$ (0.10) | PPh$_3$ (0.20) | Ag$_2$CO$_3$ (2.0) | DMF | 100° C. | 02 h | 51% |
| 03 | Pd(OAc)$_2$ (0.20) | PPh$_3$ (0.40) | Ag$_2$CO$_3$ (4.0) | DMF | 100° C. | 02 h | 64% |
| 04 | Pd(OAc)$_2$ (0.20) | PPh$_3$ (0.40) | Ag$_2$CO$_3$ (2.0) | THF | reflux | 04 h | 63% |
| 05 | Pd(OAc)$_2$ (0.10) | PPh$_3$ (0.20) | Ag$_2$CO$_3$ (2.0) | 1,4-dioxane | reflux | 03 h | 91% |
| 06 | Pd(OAc)$_2$ (0.04) | PCy$_3$ (0.08) | Cs$_2$CO$_3$ (2.0) | THF | 110° C. | 24 h | 23% |
| 07 | Pd(OAc)$_2$ (0.04) | PCy$_3$ (0.08) | K$_2$CO$_3$ (2.0) | DMF | 110° C. | 24 h | 35% |
| 08 | Pd(OAc)$_2$ (0.10) | PCy$_3$ (0.20) | Ag$_2$CO$_3$ (2.0) | DMF | 110° C. | 24 h | 31% |
| 09 | Pd(OAc)$_2$ (0.05) | PPh$_3$ (0.10) | Ag$_2$CO$_3$ (1.0) | 1,4-dioxane | 120° C. | 07 h | 90% |
| 10 | Pd(OAc)$_2$ (0.03) | PPh$_3$ (0.06) | Ag$_2$CO$_3$ (0.6) | 1,4-dioxane | 120° C. | 08 h | 89% |
| 11 | Pd(OAc)$_2$ (0.02) | PPh$_3$ (0.04) | Ag$_2$CO$_3$ (0.4) | 1,4-dioxane | 120° C. | 10 h | 93% |
| 12 | Pd(OAc)$_2$ (0.01) | PPh$_3$ (0.02) | Ag$_2$CO$_3$ (0.2) | 1,4-dioxane | 120° C. | 24 h | 72% |

Note:
Reactions shown in entries 1 and 6-12 were carried out in a sealed tube

Example 11

TABLE 2

Generalization studies of the optimized Pd-catalyzed intramolecular imine cyclization protocol

| entry | imine substrate | product | time | yield |
|---|---|---|---|---|
| 01 | (2-iodophenyl imine with N-methylsulfonyl pyrrole) | (pyrroloquinoline with NSO$_2$Me) | 08 h | 82% |
| 02 | (2-iodo-5-chlorophenyl imine with N-phenylsulfonyl pyrrole) | (chloro-pyrroloquinoline with NSO$_2$Ph) | 10 h | 70% |
| 03 | (2-iodophenyl imine with 3-substituted N-phenylsulfonyl pyrrole) | (pyrroloquinoline with PhO$_2$SN) | 05 h | 62% |

TABLE 2-continued

Generalization studies of the optimized Pd-catalyzed intramolecular imine cyclization protocol

| entry | imine substrate | product | time | yield |
|---|---|---|---|---|
| 04 | 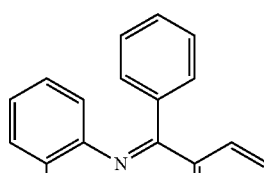 | 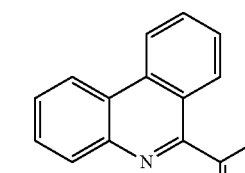 | 10 h | 90% |
| 05 | 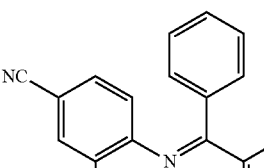 | 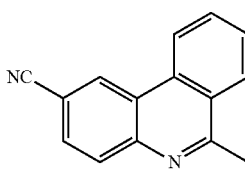 | 10 h | 85% |
| 06 | 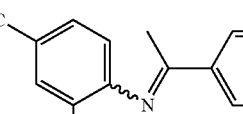 | 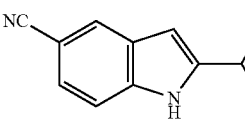 | 24 h | 51% |

Reaction condition: imine substrate (1 equiv), Pd(OAc)$_2$ (0.02 equiv), PPh$_3$ (0.04 equiv), Ag$_2$CO$_3$ (0.4 equiv), 1,4-dioxane, sealed tube, 120° C.

4-methyl-3-(methylsulfonyl)-3H-pyrrolo[2,3-e]quinoline (Table 2, entry 1)

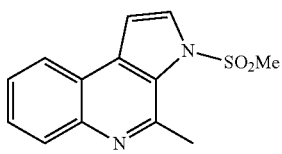 [SMILES: Cc1nc2ccccc2c2ccn(S(C)(=O)=O)c12]

Reaction Time: 8 h, R$_f$=0.50 (7:3 PE:EtOAc); MP 152-154° C., 82%; IR(Nujol): ν$_{max}$ 2928, 1459, 1377, 995, 743 cm$^{-1}$; $^1$H NMR (500 MHz, CDCl$_3$): δ 3.19 (s, 3H), 3.36 (s, 3H), 7.21 (d, J=3.6 Hz, 1H), 7.58 (t, J=8.1 Hz, 1H), 7.68 (t, J=8.3 Hz, 1H), 7.84 (d, J=3.7 Hz, 1H), 8.12 (t, J=8.5 Hz, 2H); $^{13}$C NMR (125 MHz, CDCl$_3$): δ 26.2, 43.4, 105.6, 121.7, 122.9, 126.4, 128.2, 128.3, 128.7, 131.0, 139.3, 143.4, 145.9; HRMS-ESI (m/z): calcd for [C$_{13}$H$_{12}$O$_2$N$_2$S+H]$^+$, 261.0692. found 261.0696.

Imine: HRMS-ESI (m/z): calcd for [C$_{13}$H$_{13}$O$_2$N$_2$SI+H]$^+$, 388.9815. found 388.9812.

7-chloro-4-methyl-3-(phenylsulfonyl)-3H-pyrrolo[2,3-c]quinoline (Table 2, entry 2)

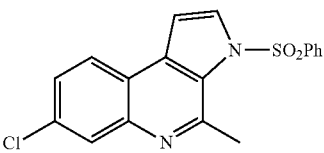

Reaction Time: 10 h, R$_f$=0.30 (9:1 PE:EtOAc); MP 178-180° C., 70%; IR(Nujol): ν$_{max}$ 2924, 2854, 2725, 1614, 1462, 1376, 822, 726, 685 cm$^{-1}$; $^1$H NMR (500 MHz, CDCl$_3$): δ 2.88 (s, 3H), 7.21 (d, J=3.7 Hz, 1H), 7.46-7.52 (m, 3H), 7.60 (t, J=7.6 Hz, 1H), 7.71 (d, J=8.5, 2H), 8.02 (s, 1H), 8.03 (d, J=6.7 Hz, 1H), 8.10 (d, J=3.7, 1H); $^{13}$C NMR (125 MHz, CDCl$_3$): δ 26.1, 105.5, 120.0, 124.2, 126.5, 126.9, 127.8, 128.6, 129.7, 132.3, 133.7, 134.3, 134.6, 139.2, 143.9, 147.9; HRMS-ESI (m/z): calcd for [C$_{18}$H$_{13}$ClN$_2$SO$_2$+H]$^+$, 357.0459. found 357.0462.

Imine: HRMS-ESI (m/z): calcd for [C$_{18}$H$_{14}$N$_2$O$_2$ClSI+H]$^+$, 484.9582. found 484.9580.

4-methyl-1-(phenylsulfonyl)-1H-pyrrolo[3,2-c]quinoline (Table 2, entry 3)

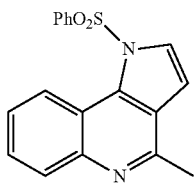

Reaction Time: 5 h, R$_f$=0.40 (4:1 PE:EtOAc); semi-solid, 62%; IR(Nujol): ν$_{max}$ 2925, 1642, 1542, 1458, 1376, 1175, 761, 726, 686 cm$^{-1}$; $^1$H NMR (400 MHz, CDCl$_3$): δ 2.85 (s, 3H), 6.93 (d, J=3.8 Hz, 1H), 7.38 (t, J=7.5 Hz, 2H), 7.42-7.51 (m, 2H), 7.52-7.61 (m, 1H), 7.72 (d, J=8.8 Hz, 2H), 7.98 (d, J=3.8 Hz, 1H), 8.07 (d, J=8.3 Hz, 1H), 8.93 (d, J=8.5 Hz, 1H); $^{13}$C NMR (100 MHz, CDCl$_3$): δ 22.5, 107.1, 117.1, 123.2, 124.5, 125.9, 126.8, 127.7, 129.0, 129.45, 129.50, 134.3, 134.6, 138.0, 145.7, 153.9; HRMS-ESI (m/z): calcd for [C$_{18}$H$_{14}$O$_2$N$_2$S+H]$^+$, 323.0849. found 323.0853.

Imine: HRMS-ESI (m/z): calcd for [C$_{18}$H$_{15}$N$_2$IO$_2$S+H]$^+$, 450.9972. found 450.9972.

6-phenylphenanthridine (Table 2, entry 4)

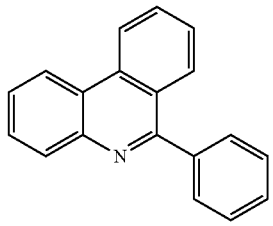 [SMILES: c1ccc(-c2nc3ccccc3c3ccccc23)cc1]

Reaction Time: 10 h, R$_f$=0.40 (19:1 PE:EtOAc); MP 104-106° C., 90%; IR(Nujol): ν$_{max}$ 2923, 2945, 2851, 1607, 1459, 1374, 760, 718, 697, 672 cm$^{-1}$; $^1$H NMR (500 MHz, CDCl$_3$): δ 7.50-7.58 (m, 3H), 7.61 (t, J=7.6 Hz, 1H), 7.65-7.80 (m, 4H), 7.86 (t, J=7.9 Hz, 1H), 8.10 (d, J=8.2, 1H), 8.26 (d, J=7.9 Hz, 1H), 8.62 (d, J=7.9 Hz, 1H), 8.71 (d, J=8.2 Hz, 1H); $^{13}$C NMR (125 MHz, CDCl$_3$): δ 121.9, 122.2, 123.8, 125.2, 126.9, 127.1, 128.4, 128.7, 128.8, 128.9, 129.7, 130.3, 130.6, 133.5, 139.6, 143.7, 161.3; HRMS-ESI (m/z): calcd for [C$_{19}$H$_{13}$N+H]$^+$, 256.1121. found 256.1121.

Imine: HRMS-ESI (m/z): calcd for [C$_{19}$H$_{14}$NI+H]$^+$, 384.0244. found 384.0244.

6-phenylphenanthridine-2-carbonitrile (Table 2, entry 5)

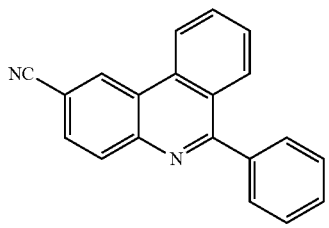 [SMILES: N#Cc1ccc2nc(-c3ccccc3)c3ccccc3c2c1]

Reaction Time: 10 h, R$_f$=0.50 (19:1 PE:EtOAc); MP 233-235° C., 85%; IR(Nujol): ν$_{max}$ 2924, 2224, 1609, 1462, 1377, 961, 829, 776, 688, 670 cm$^{-1}$; $^1$H NMR (400 MHz, CDCl$_3$): δ 7.52-7.62 (m, 3H), 7.60-7.76 (m, 3H), 7.90-7.98 (m, 2H), 8.16 (d, J=8.0 Hz, 1H), 8.29 (d, J=8.3 Hz, 1H), 8.66 (d, J=8.3 Hz, 1H), 8.95 (d, J=1.5 Hz, 1H); $^{13}$C NMR (100 MHz, CDCl$_3$): δ 110.2, 119.1, 122.2, 123.9, 125.5, 127.8, 128.5, 128.6, 129.4, 129.7, 130.4, 131.5, 131.6, 132.4, 138.9, 145.5, 164.3; HRMS-ESI (m/z): calcd for [C$_{20}$H$_{12}$N$_2$+H]$^+$, 281.1073. found 218.1075.

Imine: HRMS-ESI (m/z): calcd for [C$_{20}$H$_{13}$N$_2$I+H]$^+$, 409.0196. found 409.0193.

2-phenyl-1H-indole-5-carbonitrile (Table 2, entry 6)

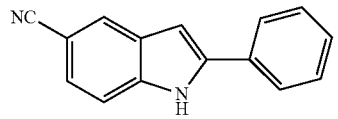 [SMILES: N#Cc1ccc2[nH]c(-c3ccccc3)cc2c1]

Reaction Time: 24 h, R$_f$=0.40 (4:1 PE:EtOAc); MP 194-196° C., 51%; $^1$H NMR (500 MHz, CDCl$_3$): δ 6.87 (d, J=1.5 Hz, 1H), 7.37-7.50 (m, 5H), 7.66 (d, J=8.5 Hz, 2H), 7.96 (s, 1H), 8.73 (brs, 1H); $^{13}$C NMR (125 MHz, CDCl$_3$): δ 100.2, 103.4, 111.7, 120.7, 125.2, 125.4, 126.0, 128.6, 129.0, 129.2, 131.2, 138.4, 140.2; HRMS-ESI (m/z): calcd for [C$_{15}$H$_{10}$N$_2$+H]$^+$, 219.0917. found 219.0917.

Imine: HRMS-ESI (m/z): calcd for [C$_{15}$H$_{11}$N$_2$I+H]$^+$, 347.0040. found 347.0042.

Example 3

Anti Malarial Activity

This study was performed in vitro on *Plasmodium falciparum* at erythrocyte stage. The test protocol for testing antimalarial activity is from R. E. Desjardins, C. J. Canfield, J. D. Haynes and J. D. Chulay *Antimicrob. Agents Chemother.* 1979, 16, 710.

A known parasite 3D7 was used, which is Chloroquine sensitive strain. 2 mg of the compound NCLite-M1 which has a molecular weight of 326.35, was dissolved in 10 mL of EtOH and used as a stock. The results are tabulated in Table 3. As seen from table 3, the compound is active at concentration as low as 2 μMoles in crude form. Further studies using highly pure compound and its soluble salts are planned.

TABLE 3

Anti malarial activity of NCLite-M1

| Sr No | Concentration | % inhibition by NCLite-M1 |
|---|---|---|
| 1 | 2-5 μM | 17.6% |
| 2 | 25 μM | 19.5% |
| 3 | 50 μM | 77.2% |
| 4 | 75 μM | 89.4% |

ADVANTAGES OF INVENTION a. Novel anti-malarial agents
b. Novel and simple synthetic process of synthesis of novel and known anti-malarial agents provided.
c. Process applicable for synthesis of other natural products

We claim:

1. A compound of formula I or a pharmaceutically acceptable salt thereof,

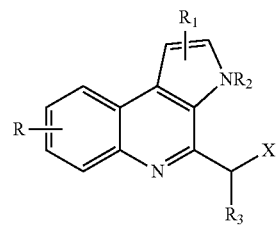

Formula I wherein R, R$_1$, and R$_2$ are selected from the group consisting of H, halide, alkyl, aryl, hetero alkyl, and hetero aryl, X is H, halide, OTf, or OTs, $R_3$ is a compound of formula III,

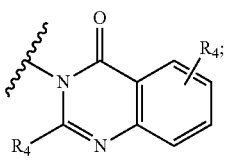

Formula III and
$R_4$ is selected from the group consisting of H, halide, alkyl, aryl, hetero alkyl, and hetero aryl.

2. A process for the preparation of compound of formula I or a pharmaceutically acceptable salt thereof as claimed in claim 1,

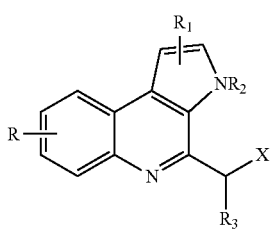

Formula I comprising the steps of:
a. refluxing a ketone of formula

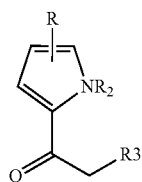

with an aniline of formula

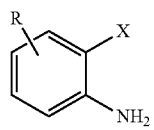

wherein R, $R_1$, $R_2$ and $R_4$ are each selected from the group consisting of H, halide, alkyl, aryl, hetero alkyl, and hetero aryl;
$R_3$ is a compound of formula III,

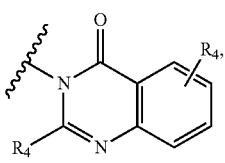

Formula III and
X is H, halide, OTf, or OTs, in mole ratio 1:1 in a solvent for a period ranging between 12-24 hrs followed by work up to obtain a corresponding imine of formula

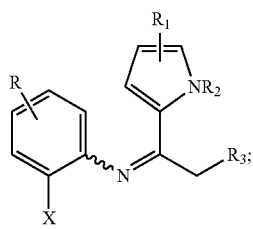

b. reacting the corresponding imine of step (a) in the presence of a Pd catalyst, a ligand, a base and a solvent at temperature ranging between 100-120° C. for a period between 8-24 hrs to obtain a compound of formula

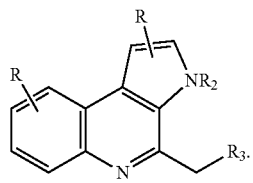

3. The process as claimed in claim 2, wherein the yield is in the range of 40% to 98%.

4. The process as claimed in claim 2, wherein the Pd catalyst is $Pd(OAc)_2$ in the range of 1 mol % to 20 mol %.

5. The process as claimed in claim 2, wherein the ligand is selected from the group consisting of triphenyl phosphate, Neocuproine and tricyclohexyl phosphine.

6. The process as claimed in claim 2, wherein the ligand is $PPh_3$ in the range of 1 mol % to 40 mol %.

7. The process as claimed in claim 2, wherein the base is selected from the group consisting of $K_2CO_3$, $Cs_2CO_3$, $Ag_2CO_3$ and KOtBu.

8. The process as claimed in claim 2, wherein the base is $Ag_2CO_3$ in the range of 1 mol % to 200 mol %.

9. The process as claimed in claim 2, wherein the solvent is selected from the group consisting of 1,4-dioxane, dry toluene, DMF, Benzene and THF.

10. A method of treating malaria comprising the step of administering a compound of formula I or a pharmaceutically acceptable salt thereof,

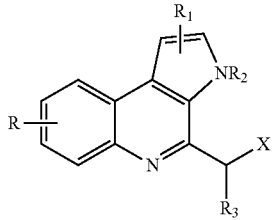

Formula I wherein R, $R_1$, and $R_2$ are selected from the group consisting of H, halide, alkyl, aryl, hetero alkyl, and hetero aryl,
X is H, halide, OTf, or OTs, $R_3$ is a compound of formula III, and
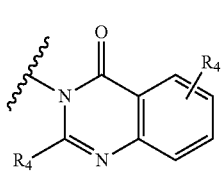
Formula III
$R_4$ is selected from the group consisting of H, halide, alkyl, aryl, hetero alkyl, and hetero aryl.
* * * * *